(12) United States Patent
Bierman et al.

(10) Patent No.: US 8,114,054 B2
(45) Date of Patent: Feb. 14, 2012

(54) MEDICAL ARTICLE ANCHORING SYSTEM

(75) Inventors: Steven F. Bierman, Del Mar, CA (US); Richard A. Pluth, San Diego, CA (US); Wayne T. Mitchell, Cardiff, CA (US)

(73) Assignee: Venetec International, Inc., Covington, GA (US)

( * ) Notice: Subject to any disclaimer, the term of this patent is extended or adjusted under 35 U.S.C. 154(b) by 0 days.

(21) Appl. No.: 12/777,207

(22) Filed: May 10, 2010

(65) Prior Publication Data

US 2010/0222748 A1    Sep. 2, 2010

Related U.S. Application Data

(62) Division of application No. 11/439,385, filed on May 23, 2006, now Pat. No. 7,722,571.

(60) Provisional application No. 60/683,925, filed on May 23, 2005, provisional application No. 60/764,917, filed on Feb. 3, 2006.

(51) Int. Cl.
*A61M 5/32* (2006.01)

(52) U.S. Cl. ........ 604/180; 604/174; 604/175; 604/176; 604/177; 604/179

(58) Field of Classification Search ........... 604/174–180
See application file for complete search history.

(56) References Cited

U.S. PATENT DOCUMENTS

| | | | |
|---|---|---|---|
| 2,525,398 A | 10/1950 | Collins | |
| 2,533,961 A | 12/1950 | Rouseau et al. | |
| 2,707,953 A | 5/1955 | Ryan | |
| 3,059,645 A | 10/1962 | Hasbrouck et al. | |
| 3,064,648 A | 11/1962 | Bujan | |
| 3,167,072 A | 1/1965 | Stone et al. | |
| 3,482,569 A | 12/1969 | Raffaelli, Sr. | |
| 3,529,597 A | 9/1970 | Fuzak | |
| 3,602,227 A | 8/1971 | Andrew | |

(Continued)

FOREIGN PATENT DOCUMENTS

DE    2341297    4/1975

(Continued)

OTHER PUBLICATIONS

Multiple-Lumen Central Venous Catheterization Product With ARROW+gard™ Antlseptic Surface (Arrow International brochure) (Apr. 1994).

*Primary Examiner* — Jackie Ho
*Assistant Examiner* — Scott Medway
(74) *Attorney, Agent, or Firm* — Knobbe Martens Olson & Bear, LLP

(57) ABSTRACT

An anchoring system provides secure attachment between a portion of a medical article and a body of a patient. The anchoring system comprises a securement device and a first fitting attached to the medical article, the first fitting having a first configuration. Embodiments of the anchoring system also comprise a second fitting attached to the medical article. The second fitting has a second configuration that differs from the first. The securement device includes a mounting surface for attaching the securement device to the patient's body and a receiving area. The receiving area is oriented so as to face away from the patient's body, and includes retainer mechanisms that are capable of engaging one or both of the first and second fittings, which have different configurations.

21 Claims, 9 Drawing Sheets

U.S. PATENT DOCUMENTS

| | | | |
|---|---|---|---|
| 3,630,195 A | 12/1971 | Santomieri | |
| 3,677,250 A | 7/1972 | Thomas | |
| 3,766,915 A | 10/1973 | Rychlik | |
| 3,812,851 A | 5/1974 | Rodriguez | |
| 3,834,380 A | 9/1974 | Boyd | |
| 3,847,370 A | 11/1974 | Engelsher | |
| 3,856,020 A | 12/1974 | Kovac | |
| 3,896,527 A | 7/1975 | Miller et al. | |
| 3,900,026 A | 8/1975 | Wagner | |
| 3,906,946 A | 9/1975 | Nordström | |
| 3,942,228 A | 3/1976 | Buckman et al. | |
| 3,973,565 A | 8/1976 | Steer | |
| 4,020,835 A | 5/1977 | Nordstrom et al. | |
| 4,057,066 A | 11/1977 | Taylor | |
| 4,059,105 A | 11/1977 | Cutruzzula et al. | |
| 4,082,094 A | 4/1978 | Dailey | |
| 4,114,618 A | 9/1978 | Vargas | |
| 4,129,128 A | 12/1978 | McFarlane | |
| 4,133,307 A | 1/1979 | Ness | |
| 4,142,527 A | 3/1979 | Garcia | |
| 4,161,177 A | 7/1979 | Fuchs | |
| 4,193,174 A | 3/1980 | Stephens | |
| 4,224,937 A | 9/1980 | Gordon | |
| 4,248,229 A | 2/1981 | Miller | |
| 4,250,880 A | 2/1981 | Gordon | |
| 4,316,461 A | 2/1982 | Marais et al. | |
| 4,324,236 A | 4/1982 | Gordon et al. | |
| 4,326,519 A | 4/1982 | D'Alo et al. | |
| 4,362,156 A | 12/1982 | Feller, Jr. et al. | |
| 4,392,853 A | 7/1983 | Muto | |
| 4,397,647 A | 8/1983 | Gordon | |
| 4,405,163 A | 9/1983 | Voges et al. | |
| 4,449,975 A | 5/1984 | Perry | |
| 4,453,933 A | 6/1984 | Speaker | |
| 4,474,559 A | 10/1984 | Steiger | |
| 4,480,639 A | 11/1984 | Peterson et al. | |
| 4,484,913 A | 11/1984 | Swauger | |
| 4,516,968 A | 5/1985 | Marshall et al. | |
| 4,517,971 A | 5/1985 | Sorbonne | |
| 4,563,177 A | 1/1986 | Kamen | |
| 4,633,863 A | 1/1987 | Filips et al. | |
| 4,645,492 A | 2/1987 | Weeks | |
| 4,650,473 A | 3/1987 | Bartholomew et al. | |
| 4,650,474 A * | 3/1987 | De Backer | 604/180 |
| 4,659,329 A | 4/1987 | Annis | |
| 4,660,555 A | 4/1987 | Payton | |
| 4,699,616 A * | 10/1987 | Nowak et al. | 604/180 |
| 4,711,636 A | 12/1987 | Bierman | |
| 4,742,824 A | 5/1988 | Payton et al. | |
| 4,808,162 A | 2/1989 | Oliver | |
| 4,823,789 A | 4/1989 | Beisang, III | |
| 4,826,486 A | 5/1989 | Palsrok et al. | |
| 4,852,844 A | 8/1989 | Villaveces | |
| 4,857,058 A | 8/1989 | Payton | |
| 4,863,432 A | 9/1989 | Kvalo | |
| 4,880,412 A | 11/1989 | Weiss | |
| 4,896,465 A | 1/1990 | Rhodes et al. | |
| 4,897,082 A | 1/1990 | Erskine | |
| 4,898,587 A | 2/1990 | Mera | |
| 4,919,654 A | 4/1990 | Kalt | |
| 4,932,943 A | 6/1990 | Nowak | |
| 4,955,864 A | 9/1990 | Hajduch | |
| 4,976,700 A | 12/1990 | Tollini | |
| 4,981,475 A * | 1/1991 | Haindl | 604/174 |
| 4,997,421 A | 3/1991 | Palsrok et al. | |
| 5,000,741 A | 3/1991 | Kalt | |
| 5,037,397 A | 8/1991 | Kalt et al. | |
| 5,073,170 A | 12/1991 | Schneider | |
| 5,084,026 A | 1/1992 | Shapiro | |
| 5,098,399 A | 3/1992 | Tollini | |
| 5,147,322 A | 9/1992 | Bowen et al. | |
| 5,147,322 A | 9/1992 | Bowen et al. | |
| 5,156,641 A | 10/1992 | White | |
| 5,192,273 A | 3/1993 | Bierman et al. | |
| 5,192,274 A * | 3/1993 | Bierman | 604/180 |
| 5,195,981 A | 3/1993 | Johnson | |
| 5,224,935 A * | 7/1993 | Hollands | 604/180 |
| 5,248,306 A | 9/1993 | Clark et al. | |
| 5,266,401 A | 11/1993 | Tollini | |
| 5,267,967 A | 12/1993 | Schneider | |
| 5,282,463 A | 2/1994 | Hammersley | |
| 5,292,312 A | 3/1994 | Delk et al. | |
| 5,304,146 A | 4/1994 | Johnson et al. | |
| 5,306,243 A | 4/1994 | Bonaldo | |
| D347,060 S * | 5/1994 | Bierman | D24/128 |
| 5,314,411 A | 5/1994 | Bierman et al. | |
| 5,322,514 A | 6/1994 | Steube et al. | |
| 5,330,438 A | 7/1994 | Gollobin et al. | |
| 5,338,308 A | 8/1994 | Wilk | |
| 5,342,317 A | 8/1994 | Claywell | |
| 5,344,406 A | 9/1994 | Spooner | |
| 5,344,414 A | 9/1994 | Lopez et al. | |
| 5,346,479 A | 9/1994 | Schneider | |
| 5,352,211 A | 10/1994 | Merskelly | |
| 5,354,282 A | 10/1994 | Bierman | |
| 5,354,283 A | 10/1994 | Bark et al. | |
| 5,368,575 A | 11/1994 | Chang | |
| 5,380,293 A | 1/1995 | Grant | |
| 5,380,294 A | 1/1995 | Persson | |
| 5,380,301 A | 1/1995 | Prichard et al. | |
| 5,382,239 A | 1/1995 | Orr et al. | |
| 5,382,240 A | 1/1995 | Lam | |
| 5,389,082 A | 2/1995 | Baugues et al. | |
| 5,395,344 A | 3/1995 | Beisang, III et al. | |
| 5,398,679 A | 3/1995 | Freed | |
| 5,403,285 A | 4/1995 | Roberts | |
| 5,413,562 A | 5/1995 | Swauger | |
| 5,443,460 A | 8/1995 | Miklusek | |
| 5,449,349 A | 9/1995 | Sallee et al. | |
| 5,456,671 A | 10/1995 | Bierman | |
| 5,468,228 A | 11/1995 | Gebert | |
| 5,468,230 A | 11/1995 | Corn | |
| 5,468,231 A | 11/1995 | Newman et al. | |
| 5,470,321 A | 11/1995 | Forster et al. | |
| D364,922 S | 12/1995 | Bierman | |
| 5,484,420 A | 1/1996 | Russo | |
| 5,496,282 A | 3/1996 | Militzer et al. | |
| 5,496,283 A | 3/1996 | Alexander | |
| 5,499,976 A | 3/1996 | Dalton | |
| 5,520,656 A | 5/1996 | Byrd | |
| 5,522,803 A | 6/1996 | Teissen-Simony | |
| 5,527,293 A | 6/1996 | Zamierowski | |
| 5,549,567 A | 8/1996 | Wolman | |
| D375,355 S | 11/1996 | Bierman | |
| 5,578,013 A | 11/1996 | Bierman | |
| 5,637,098 A | 6/1997 | Bierman | |
| 5,643,217 A | 7/1997 | Dobkin | |
| 5,681,290 A | 10/1997 | Alexander | |
| 5,685,859 A | 11/1997 | Kornerup | |
| 5,693,032 A | 12/1997 | Bierman | |
| 5,702,371 A | 12/1997 | Bierman | |
| D389,911 S | 1/1998 | Bierman | |
| 5,722,959 A | 3/1998 | Bierman | |
| 5,735,822 A | 4/1998 | Steins | |
| 5,792,115 A | 8/1998 | Horn | |
| 5,795,335 A | 8/1998 | Zinreich | |
| 5,800,402 A | 9/1998 | Bierman | |
| 5,810,781 A | 9/1998 | Bierman | |
| D399,954 S | 10/1998 | Bierman | |
| 5,827,239 A | 10/1998 | Dillon et al. | |
| 5,833,667 A | 11/1998 | Bierman | |
| 5,855,591 A | 1/1999 | Bierman | |
| 5,989,213 A | 11/1999 | Maginot | |
| 6,001,081 A | 12/1999 | Collen | |
| 6,117,163 A | 9/2000 | Bierman | |
| 6,132,398 A | 10/2000 | Bierman | |
| 6,213,979 B1 | 4/2001 | Bierman | |
| 6,224,571 B1 | 5/2001 | Bierman | |
| 6,231,548 B1 | 5/2001 | Bassett | |
| 6,283,945 B1 | 9/2001 | Bierman | |
| 6,290,265 B1 | 9/2001 | Warburton-Pitt et al. | |
| 6,290,676 B1 | 9/2001 | Bierman | |
| 6,361,523 B1 | 3/2002 | Bierman | |
| 6,428,513 B1 | 8/2002 | Abrahamson | |
| 6,428,515 B1 * | 8/2002 | Bierman et al. | 604/174 |
| 6,447,485 B2 | 9/2002 | Bierman | |
| 6,491,664 B2 | 12/2002 | Bierman | |

| | | | | | |
|---|---|---|---|---|---|
| 6,572,588 | B1 | 6/2003 | Bierman et al. | | |
| 6,582,403 | B1 | 6/2003 | Bierman et al. | | |
| 6,929,625 | B2 | 8/2005 | Bierman | | |
| 6,979,320 | B2 | 12/2005 | Bierman | | |
| 7,018,362 | B2 | 3/2006 | Bierman et al. | | |
| 7,223,256 | B2 | 5/2007 | Bierman | | |
| 7,284,730 | B2 | 10/2007 | Walsh et al. | | |
| 7,572,274 | B2 * | 8/2009 | Yassinzadeh | | 606/213 |
| D615,649 | S * | 5/2010 | Zinn et al. | | D24/130 |
| 2002/0026152 | A1 | 2/2002 | Bierman | | |
| 2002/0165493 | A1 | 11/2002 | Bierman | | |
| 2004/0097903 | A1 * | 5/2004 | Raulerson | | 604/523 |
| 2005/0038453 | A1 * | 2/2005 | Raulerson | | 606/151 |
| 2006/0129103 | A1 | 6/2006 | Bierman et al. | | |
| 2006/0276752 | A1 | 12/2006 | Bierman et al. | | |

FOREIGN PATENT DOCUMENTS

| | | |
|---|---|---|
| EP | 0 064 284 | 11/1982 |
| EP | 0 247 590 | 12/1987 |
| EP | 0 356 683 | 3/1990 |
| EP | 0 931 560 | 7/1999 |
| FR | 1184139 | 7/1959 |
| FR | 2381529 | 9/1978 |
| GB | 2063679 | 6/1981 |
| GB | 2086466 | 5/1982 |
| GB | 2288542 A | 10/1995 |
| WO | WO 80/01458 | 7/1980 |
| WO | WO 85/02774 | 7/1985 |
| WO | WO 94/12231 | 6/1994 |
| WO | WO 96/26756 | 9/1996 |

* cited by examiner

MEDICAL ARTICLE ANCHORING SYSTEM

RELATED APPLICATIONS

This application is a divisional of application Ser. No. 11/439,385, filed May 23, 2006 now U.S. Pat. No. 7,722,571, entitled "MEDICAL ARTICLE ANCHORING SYSTEM", which claims the benefit of U.S. Provisional Application No. 60/683,925, filed May 23, 2005, and U.S. Provisional Application No. 60/764,917, filed Feb. 3, 2006, all of which are hereby incorporated by reference in their entireties.

BACKGROUND OF THE INVENTION

1. Field of the Invention

The present invention relates in general to an anchoring system for securing a medical article to a patient and, in particular, to an anchoring system for securing a medical article to a patient to inhibit movement or migration of the medical article relative to the patient.

2. Description of the Related Art

It is common in health care settings to attach medical articles to the skin of patients to facilitate their treatment. For example, catheters are often used to introduce fluids and medications directly into the patient or to withdraw fluids from the patient. Other catheters may be used to perform certain types of medical procedures and diagnostic analysis. One example of a typical catheter is an intra-aortic balloon (IAB) catheter, which is used to assist the heart in delivering oxygen.

Catheters often remain in place for many days. In order to secure the catheter in position at the insertion site, the healthcare worker often secures the catheter to the patient using tape. That is, the healthcare worker commonly places long pieces of tape across the portion of the catheter near the insertion site in a crisscross pattern to secure the catheter to the patient's skin. This securement inhibits disconnection between the catheter and the insertion site, and also prevents the catheter from snagging on the bed rail or other objects.

Tape, however, often collects dirt and other contaminants. Normal protocol therefore requires periodic (e.g., daily) tape changes to inhibit bacteria and germ growth at the securement site. These frequent tape changes often excoriate the patient's skin. Additionally, valuable time is spent by healthcare workers applying and reapplying the tape. Because many healthcare workers find the taping procedure cumbersome and difficult to accomplish when wearing gloves, they often remove their gloves when taping. Not only does this increase the amount of time spent on the taping procedure, but it also subjects the healthcare worker to an increased risk of infection. Moreover, even if healthcare workers remain gloved, contact between the adhesive surface of the tape and the latex gloves can cause micro-holes in the gloves, subjecting the healthcare worker to possible infection.

A variety of catheter securement devices have been developed to obviate the need for frequent application of tape to secure a catheter to a patient. One such securement device provides a flexible clamp with winged extensions that are sutured to the patient's skin. In some applications, the winged extensions are integrally formed with the catheter. In other applications, the flexible clamp is covered by a rigid fitting (e.g., a box clamp), which receives the catheter/clamp combination in a friction-fit manner. The rigid fitting and flexible clamp are formed with lateral, aligned holes, which allow the combination to be sutured to the patient's skin. Although these suturing devices function to attach the catheter to the patient, it is obviously painful and uncomfortable for the patient. These devices are also time consuming and inconvenient to secure, pose the risk of needle-stick to the health care provider, and risk suture-site infection to the patient.

In addition, suture material tends to exhibit poor gripping on medical tubes and can cut through the winged extension of the flexible clamp if a rigid clamp is not used. However, the use of a rigid fitting complicates the securement procedure by adding yet another component that can be dropped on the floor and become unsterile. In addition, the sutured securement of the flexible clamp and/or the rigid fitting assembly does not permit easy release of the catheter from the patient for dressing changes and insertion site cleaning. A removal instrument (e.g., sterile scissors) also is generally required for suture removal.

Rather than suturing lateral, aligned holes to a patient's skin, other catheter securement devices provide an adhesive layer or resilient band interposed between the flexible clamp and the patient's skin. See, for example, U.S. Pat. Nos. 5,342,317; 5,084,026; 4,449,975; and 4,250,880. Many of these securement devices, however, suffer from one or more of the following disadvantages: are time consuming and inconvenient to secure; have multiple parts, which can be dropped and become unsterile; and require removal instruments (e.g., hemostat or scissors) to disengage the catheter from the securement device.

Additionally, no standard exists regarding spacing of the lateral holes of the catheters and catheter fittings, or the shapes of the catheters and fittings. Manufacturers invariably produce catheters and catheter fittings with holes having varying geometries and distances therebetween. Prior securement devices thus become dedicated to fit and secure only certain catheter fittings.

SUMMARY OF THE INVENTION

An aspect of the present invention involves a simply-structured anchoring system that secures a medical article in a fixed position, but easily releases the medical article for dressing changes or other servicing. The anchoring system also can cooperate and engage multiple catheter fittings disposed on the same or different catheters, and thereby facilitates different configurations for the system on the patient's body. In particular, the anchoring system may be used with a variety of catheters and/or catheter fittings which have varying geometries. The anchoring system also provides a technique for anchoring medical articles to a patient in a fixed position and allowing for the release of those articles.

In one preferred form of this aspect of the invention, the anchoring system comprises a fitting attached to the medical article, the fitting extending laterally beyond the medical article and a securement device. The securement device includes a mounting surface for attaching the securement device to the patient's body, a receiving area oriented so as to face away from the patient's body, and at least two clips engaging the fitting around a perimeter of the fitting. The securement device preferably includes at least three clips, and more preferably includes four clips.

Another aspect of the present invention involves a securement device for anchoring a fitting of a medical article to a body of a patient. The securement device includes a mounting surface for attaching the securement device to the patient's body, a receiving area oriented so as to face away from the patient's body, and one or more clips engaging the fitting around a perimeter of the fitting. In one embodiment, the clip can extend upward relative to the mounting surface and adjacent to a peripheral edge of the fitting, over a section of the fitting, and latch over an opposing peripheral edge of the fitting. In another preferred embodiment, the securement device includes at least two clips disposed apart from each other. The securement device preferably includes at least three clips, and more preferably includes at least four clips. In a more preferred form, the securement device can also include one or more covers that extend over at least a portion of the fitting when retained by the securement device.

In accordance a preferred method of securing a medical article to a body of a patient, a securement device is located over the skin a the patient at a desired located on the patient's body. The securement device includes an adhesive-coated mounting surface for attaching the securement device to the patient's body and a receiving area. The securement device is oriented on the patient's body so as to face away from the patient's body to expose the receiving area and one or more clips. In a preferred embodiment, the securement device includes a plurality of clips (i.e., two or more). The clips are disposed generally around the receiving area and are spaced apart from one another. At least some of the clips are arranged so as to generally correspond to the shape of a portion of the medical device to be retained. A portion of the medical article is then engages with at least two of the plurality of the clips to attached the portion to the securement device. The securement device is adhered to the body of the patient using the mounting surface.

Another aspect of the present invention involves an anchoring system for securing a medical article to a body of a patient that comprises a first fitting attached to the medical article, having a first configuration, a second fitting attached to the medical article, having a second configuration that differs from the first configuration, and a securement device. The securement device includes a mounting surface for attaching the securement device to the patient's body and a receiving area oriented so as to face away from the patient's body. The receiving area includes a plurality of retainer mechanisms. At least one of the retainer mechanisms is configured to engage the first fitting and at least another of the retainer mechanisms is configured to engage the second fitting.

An additional aspect of the present invention involves an anchoring system for securing a medical article to a body of a patient. The anchoring system comprises a first fitting attached to the medical article, the first fitting extending laterally beyond the medical article, having a narrower longitudinal cross-section in a connecting region proximate to the medical article and having a plurality of holes disposed on a wing region proximate to a lateral edge, a second fitting attached to the medical article, the second fitting extending laterally beyond the medical article, having a narrower lateral cross-section than the first fitting, and having a wider longitudinal cross-section in a second connecting region proximate to the medical article, and a securement device. The securement device comprises a mounting surface for attaching the securement device to the patient's body and a receiving area oriented so as to face away from the patient's body. The receiving area includes a plurality of posts configured to extend through the plurality of holes of the first fitting, a plurality of clips configured to engage the second fitting but not engage the first fitting, and at least one cover. The cover is moveable relative to the receiving area so as to move between an open position and a closed position. The cover lies at least partially above at least one of the plurality of posts in the closed position.

A further aspect of the present invention involves an anchoring system for securing a medical article to a body of a patient. The anchoring system comprises a plurality of fittings attached to the medical article and a securement device. The securement device includes a mounting surface for attaching the securement device to the patient's body and a receiving area oriented so as to face away from the patient's body. The receiving area including a first securement means for engaging at least one of the plurality of fittings and a second securement means for engaging at least one other of the plurality of fittings.

In accordance with another preferred method of securing a medical article to a body of a patient, a securement device is provided having a mounting surface and a receiving area. The securement device is oriented on the body of the patient such that the receiving area faces away from the patient's body. Either a first securement mechanism and a second securement mechanism, both of which are disposed on the receiving area, is selected to engage the medical article based upon a medical article insertion site. The method further comprises engaging the selected one of the first securement mechanism and second securement mechanism with a fitting attached to the medical article and securing the securement device to the body of the patient using the mounting surface.

A further aspect of the present invention involves a securement device for anchoring a fitting on a medical article to a body of a patient. The securement device includes a mounting surface for attaching the securement device to the patient's body and a retainer that is at least partially disposed on the mounting surface. The retainer comprises a base and a plurality of clips that extend from the base. The clips are spaced apart by a distance that substantially equals a distance across a portion of the fitting, and each clip includes an abutment portion to abut against a corresponding edge of the fitting. Each clip also includes a tang. The tang is disposed above the base by a distance greater than a transverse thickness of the fitting at the corresponding edge. At least one of the clips is disposed adjacent to a generally longitudinally facing surface of the fitting to inhibit at least longitudinal movement of the fitting relative to the retainer.

The systems and methods of the invention have several aspects and features, no single one of which is solely responsible for all of its desirable attributes. Without limiting the scope of the invention as expressed by the claims, its more prominent aspects have been discussed briefly above. Further aspects and features will also be understood from the description below. Additionally, various aspects and features of the system can be practiced apart from each other. For example, while several of the above-noted aspects of the invention involve an anchoring system that includes at least one securement device and at least one fitting of a medical article, the securement device itself can form a separate aspect of the present invention.

BRIEF DESCRIPTION OF THE DRAWINGS

These and other features, aspects and advantages of the present invention will now be described in connection with preferred embodiments of the invention, in reference to the accompanying drawings. The illustrated embodiments, however, are merely examples and are not intended to limit the invention. The following are brief descriptions of the drawings.

DETAILED DESCRIPTION OF THE PREFERRED EMBODIMENTS

Figure 1:
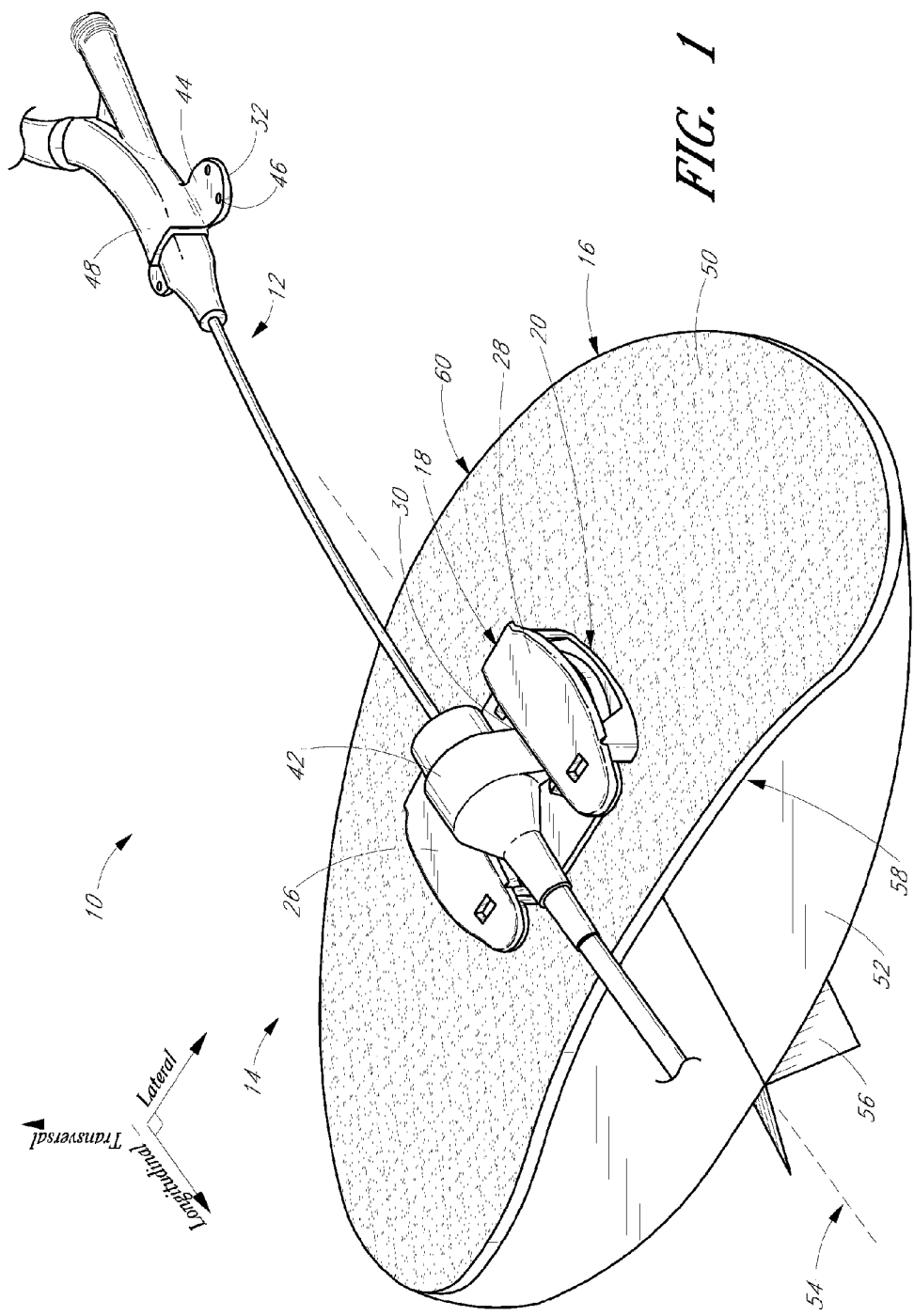
FIG. 1 is a perspective view of a medical article anchoring system that is configured in accordance with a preferred embodiment of the present invention, with a medical article illustrated in a first inserted position and with covers of the anchoring system shown in a closed position.
Figure 2:
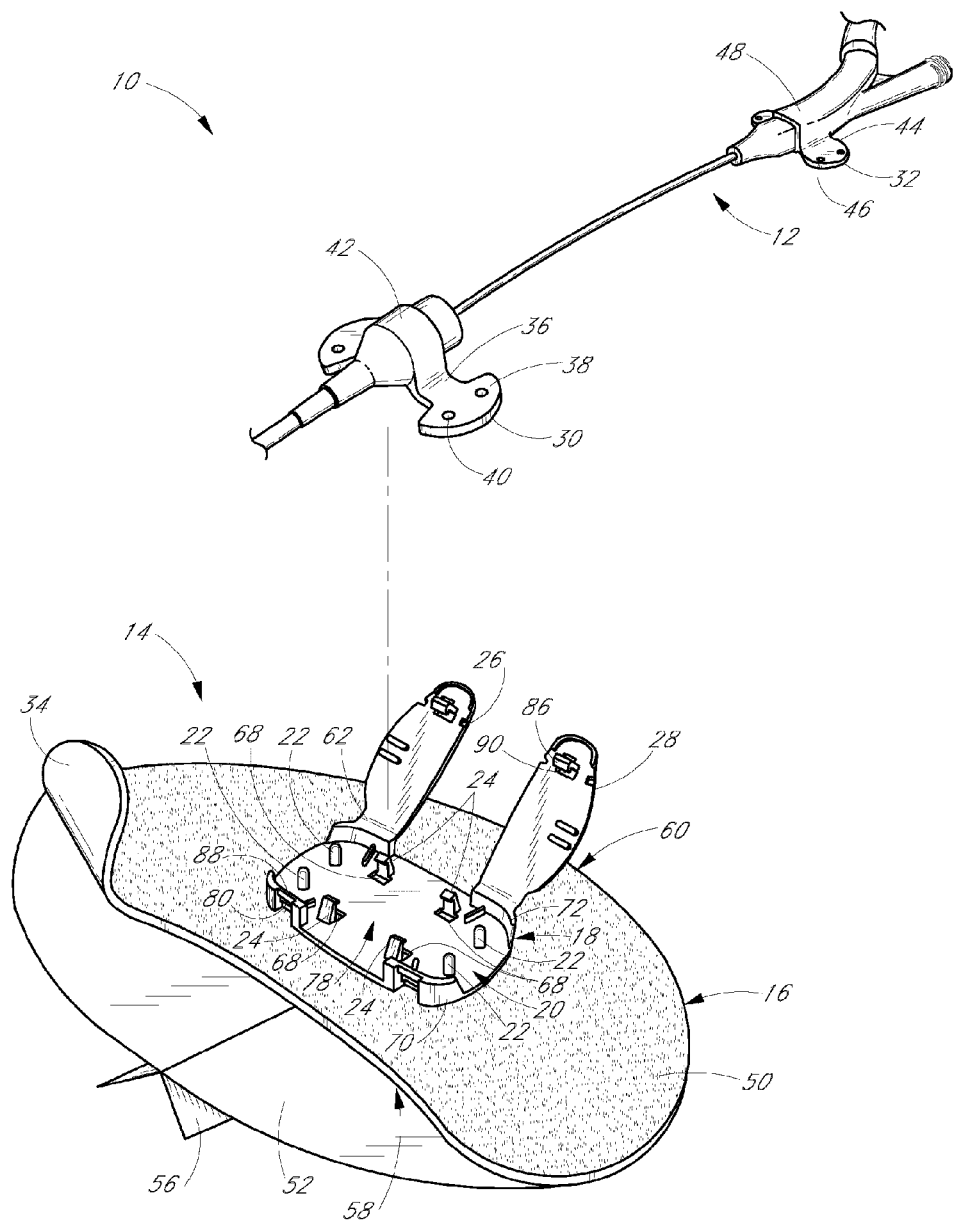
FIG. 2 is a perspective view of the medical article anchoring system of FIG. 1 with the medical article removed and with a corner of an anchor pad turned up to illustrate its lower surface.
Figure 9:
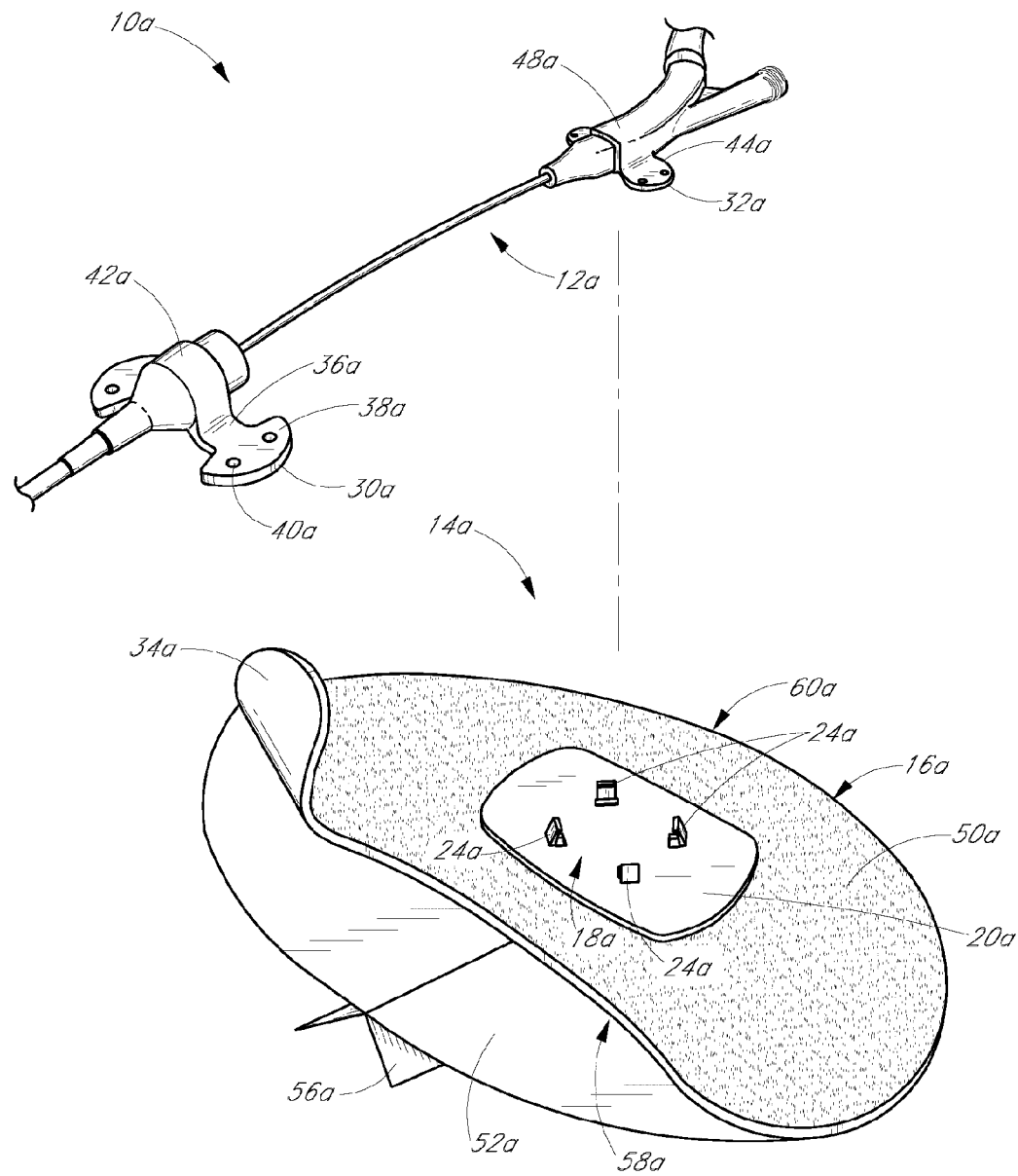
FIG. 9 is a perspective view of another embodiment of a medical article anchoring system with the medical article removed, with a corner of an anchor pad turned up to illustrate its lower surface.
Figure 12:
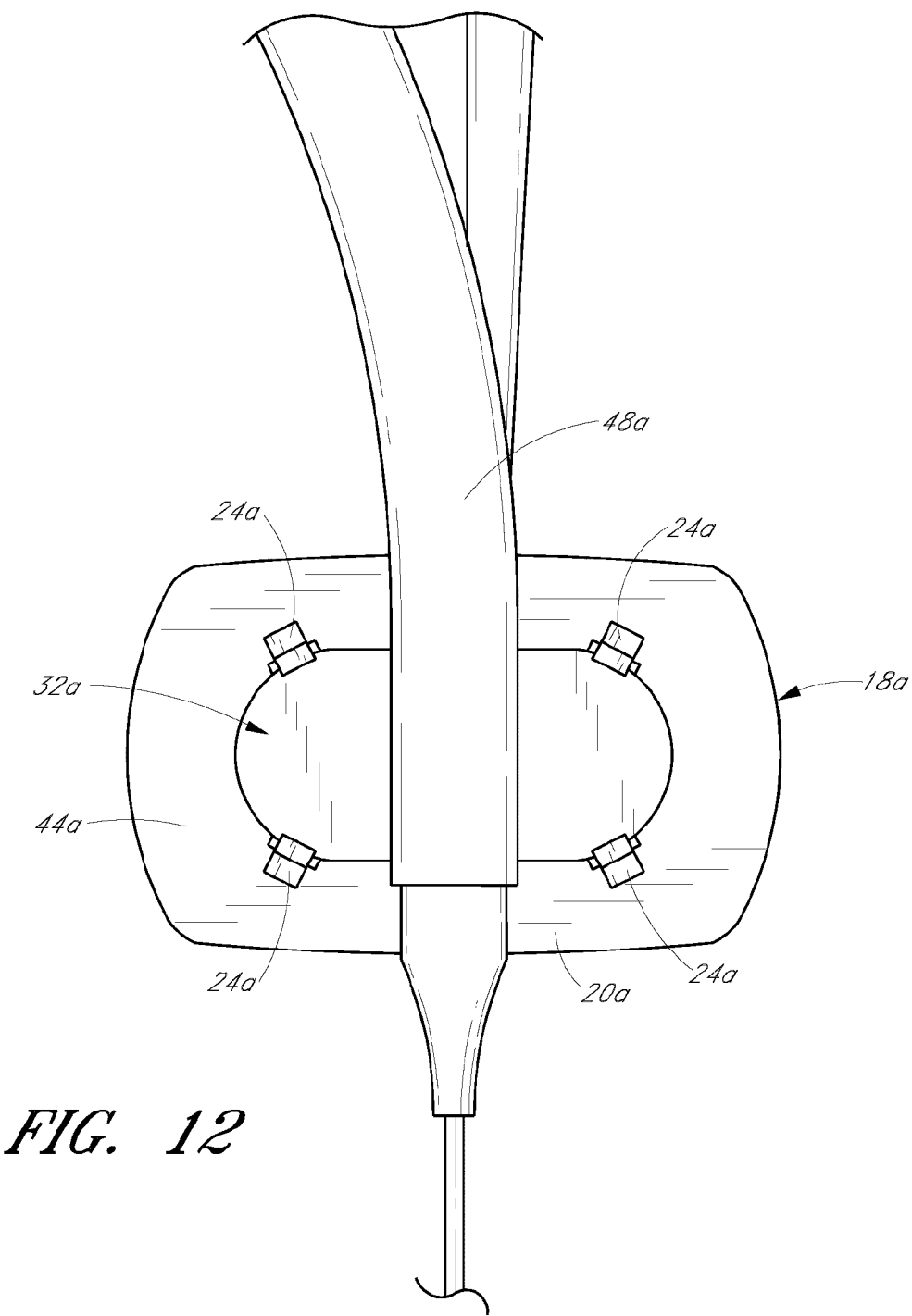
FIG. 12 is an enlarged top plan view of the medical article of FIG. 9 inserted in the retainer and retained by the plurality of clips.

One embodiment of a medical article anchoring system, which is generally designated by reference numeral 10 in FIG. 1, is disclosed in the context of use with an exemplary medical article (as shown in FIGS. 1 and 2 as an intra-aortic balloon (IAB) catheter and designated by reference numeral 12). A second embodiment of the medical article anchoring system, which is designated by reference numeral 100 in FIG. 9, is disclosed in the context of use with another exemplary medical article (as shown in FIGS. 9 and 12 as a variant of the IAB catheter and designated by the reference numeral 112). The principles of the present invention, however, are not limited to securement of catheters, much less to the securement of an IAB catheter. Instead, it will be understood by one of ordinary skill in this art, in view of the present disclosure, that the anchoring systems and/or retainers disclosed herein also can be successfully utilized in connection with other types of medical articles, including, but not limited to, other types of catheters, fluid drainage and delivery tubes and electrical wires. For example, but without limitation, the retainers disclosed herein also can be configured to receive and secure peripheral catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors. One skilled in the art may also find additional applications for the devices and systems disclosed herein. Thus, the illustrations and descriptions of the anchoring systems in connection with an IAB catheter and variants thereof are merely exemplary of two possible applications of the anchoring systems.

The anchoring system according to one aspect of the invention enables releasable engagement of the catheter to the patient, as illustrated by the embodiments described herein. The releasable engagement is achieved by cooperation among a base, at least one cover and at least one post element, or by cooperation among a base and at least one clip or a plurality of clips. This cooperation allows the catheter to be disconnected from the securement device and from the patient, for any of a variety of known purposes. For instance, the healthcare worker may want to remove the catheter from the securement device to ease disconnection of the catheter from the insertion point or to clean the patient. The disengagement of the catheter from the securement device, however, can be accomplished without removing the securement device from the patient.

The securement device, in accordance with one aspect of the invention, arrests movement of the catheter and/or catheter fitting in the transverse direction to hold the catheter and/or catheter fitting on the patient. Preferably, the securement device also arrests longitudinal movement of the catheter and, most preferably it additionally arrests longitudinal movement of the catheter and/or catheter fitting. Additionally, the anchoring system can include multiple securement devices with each one configured to arrest movement of the catheter and/or catheter fitting in at least one or more of the directions. One embodiment of the present anchoring system accordingly inhibits axial or longitudinal movement of the catheter with respect to the securement device, and hence, with respect to the insertion site on the patient. In an embodiment illustrated in FIG. 7, the base and cover assembly surround the catheter and/or catheter fitting while the post(s) extends through a corresponding suture or mount opening(s) formed on the catheter and/or catheter fitting. Transverse and lateral movement is generally arrested by the holding effect provided by the base and cover assembly. Longitudinal movement is arrested by the interaction between the post(s) and the opening(s). In an embodiment illustrated in FIG. 8, the clip(s) surround the catheter and/or catheter fitting. Longitudinal and transverse movement is generally arrested by the holding effect provided by the clip(s). This holding effect may also arrest lateral movement. Additional features of the retainer may also arrest lateral movement. For example, the base or cover may include a post or wall disposed to contact or inhibit movement of the medical article in the lateral direction. In an embodiment, the clip(s) inhibit longitudinal and transverse movement of the catheter and/or catheter fitting, while the wall(s) inhibit lateral movement.

In accordance with another form of the securement device, a plurality of clips (e.g., two, three or four) are located on the base and are positioned relative to the lateral and/or longitudinal directions so as to interpose the catheter and/or catheter fitting and to thus inhibit lateral and/or longitudinal movement, respectively. The clips can also fit into or engage the structure of the catheter fitting (e.g., fit within a notch on the catheter fitting). In the illustrated embodiment shown in FIG. 9, four clips surround the catheter fitting to inhibit such movement. Portions of the four clips located above the catheter and/or catheter fitting inhibit transverse movement relative to the retainer. For example, one of the four clips includes a hook portion spaced from the base by a sufficient distance to accommodate at least a portion of the catheter and/or catheter fitting between the base and the hook portion so as to thereby inhibit movement of the fitting in the transverse direction.

In one preferred form, the present anchoring system also is adapted to cooperate with at least two different style fittings. In particular, the medical article anchoring system 10 includes clips as well as posts in different configurations in order to engage differently configured fittings of the medical article. This feature can also be used to accommodate catheters with catheter fittings having different sizes and/or shapes. So configured, a healthcare professional can choose between varying insertion sites and attachment sites for the securement device based on the different fittings available. Various other aspects of the present invention, however, can be used apart from this "dual-securement" feature, as will be apparent from the discussion of the embodiments below.

To assist in the description of these components of the embodiments of the anchoring system (see FIGS. 1 and 9); the following coordinate terms are used. A "longitudinal axis" is generally parallel to the section of the catheter or medical article lying across the securement device. A "lateral axis" is normal to the longitudinal axis and is generally parallel to the plane of the anchor pad. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal," which are used to describe the present anchoring system, are used consistently with the description of the exemplary applications. Thus, proximal and distal are used in reference to the center of the patient's body, and proximal is used to express greater proximity to that center. The terms "upper," "lower," "top," "bottom," and the like, which also are used to describe the present anchoring system, are used in reference to the illustrations of the embodiments. "Front" and "back" are used in reference to the proximal and distal sides of an article (or an element of the article), respectively. A detailed description of embodiments of the anchoring system, and their associated method of use, now follows.

Dual-Securement Anchoring System

With reference to FIGS. 1 and 2, the anchoring system 10 is constructed in accordance with a preferred embodiment of the present invention. The system comprises a medical device, such as a catheter 12, and a securement device 14. The securement device 14 further comprises an anchor pad 16, upon which rests a retainer 18. The retainer 18 may be configured in a number of different ways. In the illustrated embodiment, the base 20 of the retainer 18 supports four posts 22 and four clips 24. Two covers 26, 28 also extend from the retainer 18 and can be moved between open and closed positions. FIG. 1 illustrates the covers 26, 28 in closed positions, and FIG. 2 illustrates the covers 26, 28 in open positions. The retainer 18 is configured to accept, to retain and to secure one or both catheter fittings 30, 32 within the securement device 14.

As illustrated in FIG. 1, with the catheter 12 in a first inserted position, the first fitting 30 may be coupled with the base 20 of the retainer 18, while the covers 26, 28 extend in a closed position over at least a portion of the first fitting 30. As illustrated, there are two covers 26, 28 in the present embodiment, each independently attached to the base 20. Once the first fitting 30 is positioned on the base 20, the covers 26, 28 are moved into a closed position over the base 20 and first fitting 30 to inhibit transverse motion of the first fitting 30. The fitting 30 is retained longitudinally (and preferably also laterally) by its interaction with one or more upstanding structures of the retainer 18, as well as by its interaction with the surrounding sections of the base 20 and/or the covers 26, 28. In the illustrated embodiment, the upstanding structures are posts 22; however, clips, abutments or the like can also be used. The covers 26, 28 extend in a closed position over at least a portion of the upstanding structures (e.g., over at least portion of the four posts 22).

Each component of the present anchoring system 10 is affixed to another, and in turn to a patient's body in one method of application. The anchor pad 16 is securely attached to the skin of the patient by its lower surface, while the retainer 18 is securely attached to the upper surface of the anchor pad 16. Either of these attachment functions may be provided by a number of different mechanisms well known to those of skill in the art. As will be discussed in more detail below, mechanical and chemical (e.g. stitches or adhesives) means may be employed in this regard.

As shown in FIG. 1 in a first inserted position, the catheter 12 may be, in turn, securely attached to the retainer 18 by means of the first fitting 30. As each of these components lies in fixed orientation to another, the anchoring system 10 can, if located appropriately, place the catheter 12 in a fixed orientation and position with respect to an insertion site at which a portion of the catheter 12 enters the patient's body. In one conventional application, the insertion site would lie further forward, in a proximal direction, from the location of the securement device 14.

In FIG. 2, the same anchoring system 10 is shown in a disassembled view such that the catheter 12 and securement device 14 are in an unattached state. In addition, a portion of the anchor pad 16 is turned up to illustrate its lower surface 34. The following describes each component of the illustrated anchoring system 10 in greater detail.

Catheter

As described above, the catheter 12 that forms a component of the anchoring system 10 may be one of a number of different medical devices. In a illustrated embodiment, shown in FIGS. 1 and 2, the medical device is an IAB catheter 12, such as the IAB catheter manufactured by Datascope®. In one embodiment, each of two fittings 30, 32 having different configurations can be attached to the catheter 12. The first fitting 30 is located along the longitudinal axis in a proximal direction from the second fitting 32. The first and second fittings 30, 32 can be located at different locations along other axes to provide different location and securement options. In another embodiment, for example, the fittings 30, 32 might be provided along different positions on the lateral axis, allowing "off-axis" attachment of the securement device 14 from the longitudinal axis of the catheter 12. This embodiment might facilitate insertion of medical devices in more inaccessible regions of the body. In the illustrated embodiment, the two fittings 30, 32 are fixed to the body of the catheter 12; however, in other applications, one or more of the fittings can be removable attached to the catheter body.

In the illustrated embodiment, the two fittings 30, 32 are provided such that the securement device 14 may be located at varying distances in the longitudinal direction from the insertion site. Either of these two fittings 30, 32 can be releasably engaged with the securement device 14.

In other embodiments, more than two fittings may be used in conjunction with the catheter 12, providing further options for varying the distances, orientations, and configurations of the catheter 12 with respect to the attachment and insertion sites.

In still other embodiments, only one fitting may be provided on the catheter 12. As in the case of multiple fittings, this fitting may be configured to engageably interact with the securement device 14, thereby providing fixation between the catheter 12 and the patient's body.

In a preferred embodiment, illustrated in FIGS. 1 and 2, the first fitting 30 lies farther forward in a proximal direction along the longitudinal axis of the catheter 12. The first fitting 30 comprises a connecting portion 36 near to the lumen of the catheter 12, which has a narrow longitudinal cross-sectional width. The first fitting 30 further comprises at least one wing portion 38, which extends from the connecting portion 36 and flares out in the longitudinal direction. Disposed on the wing portions 38 are holes 40. The holes 40 are suitably disposed on the wing portions 38. The posts 22 of the securement device 14 are sized to fit within the holes.

The first fitting 30 is attached to the catheter 12 by a cylindrical attachment 42 that grips and secures the catheter 12 with respect to the first fitting 30. Alternative configurations of the first fitting 30 are, of course, possible. Depending upon the securement mechanisms provided by the securement device 14, the first fitting 30 can take on a variety of configurations that can provide sufficient attachment. In some embodiments, the first fitting 30 may not be necessary to secure the catheter 12 to the securement device 14 at different locations, as the catheter 12 itself may provide the corresponding fitting (e.g., one similar to the first fitting 30).

In a preferred embodiment, illustrated in FIGS. 1 and 2, the second fitting 32 lies farther back in a distal direction along the longitudinal axis of the catheter 12. The second fitting 32 comprises at least one wing portion 44 near the lumen of the catheter 12. The wing portion 44 has a broad longitudinal cross-sectional width in comparison with the longitudinal cross-section of the connecting portion 36 of the first fitting 30. In one embodiment, the second fitting 32 further comprises at least one hole 46. Although the four illustrated holes 46 are not employed in the present embodiment to provide securement, different securement devices may facilitate such a connection.

The second fitting 32 is attached to the catheter 12 by a housing 48 that grips and secures the catheter 12 with respect to the second fitting 32. The retainer 18 includes a plurality of clips 24 and/or walls 25 which together inhibit the retained portion of the catheter 12 from moving in the longitudinal, transverse, and/or lateral directions. Alternative configurations of the second fitting 32 are, of course, possible. Depending upon the securement mechanisms provided by the securement device 14, the second fitting 32 can take on a variety of configurations that can provide sufficient attachment. In some embodiments, the second fitting 32 may not be necessary to secure the catheter 12 to the securement device 14 at different locations, as the catheter 12 itself may provide the corresponding fitting (e.g., one similar to the second fitting 32). In other embodiments, the first fitting 30 may slide longitudinally along the catheter 12, possibly obviating the need for a second fitting.

The fittings 30, 32 suitably are made of a strong, but flexible material. Suitable materials which are both sufficiently strong but flexible include without limitation: plastics, polymers, or composites such as polypropylene, polyethylene, polycarbonate, polyvinylchloride, acrylonitrile butadiene styrene, styrene butadiene, nylon, olefin, acrylic, polyester, moldable silicon, thermoplastic urethane, thermoplastic elastomers, thermoset plastics and the like. The fittings 30, 32 are suitably formed by injection molding using a styrene butadiene polymer, such as KRO3 resin, available commercially from Phillips Petroleum of Houston, Tex. However, other materials can be used.

The fittings 30, 32 may also be of a unitary piece with the body of the catheter 12, or formed separately from the line and permanently or releasably attached to the catheter 12. In the illustrated embodiments, the fittings 30, 32 are formed separately from the catheter 12, but are also permanently attached to the catheter 12. In other embodiments, the fittings 30, 32 and catheter 12 may be formed as one piece to reduce manufacturing costs, while in other embodiments, the fittings 30, 32 and catheter 12 may be releasably attached to add further flexibility to the attachment and insertion options.

Anchor Pad

FIG. 2 is a perspective view of the medical article anchoring system of FIG. 1 with a corner of an anchor pad 16 turned up to illustrate its lower surface. The lower side of the pad 16 faces toward the skin of the patient, and is suitably covered with an adhesive surface suitable for attaching the anchor pad 16 to the skin of the patient. The entire surface, however, need not be covered. An upper surface 50 of the anchor pad 16 faces away from the skin of the patient and supports the retainer 18.

The anchor pad 16 can also include a concave section 58 that narrows the center of the anchor pad 16 proximate to the retainer 18. In the illustrated embodiment of FIG. 2, the anchor pad 16 is formed generally into a crescent shape that includes a concave section 58 on one side of the retainer and a slightly convex section 60 on the other. This shape permits the pad 16 to be placed on the patient such that the arms of the crescent extend towards (as illustrated) or away from the insertion site, depending upon the application. This shape of the anchor pad 16, however, is merely an example.

In the illustrated embodiment, the retainer 18 is centered upon the anchor pad 16 about the centerline 54, which bifurcates the crescent shape. As illustrated, the lateral sides of the anchor pad 16 have more contact area, both forward and rearward of the retainer 18 in the longitudinal direction, which provides greater stability and adhesion to a patient's skin while still permitting the retainer 18 to be located relatively near the insertion site. Although not illustrated, the anchor pad 16 also can include suture and/or breather holes to the sides of the retainer 18. Although only a single shape of the anchor pad is illustrated in FIG. 2, those of skill in the art will recognize that a variety of shapes can be used.

The anchor pad 16 can comprise a laminate structure with an upper plastic (e.g., woven polyester), paper, or foam layer (e.g., closed-cell polyethylene foam) and a lower adhesive layer. The lower adhesive layer constitutes a lower surface 34 of the anchor pad. The lower surface 34 desirably is a medical-grade adhesive and can be either diaphoretic or nondiaphoretic, depending upon the particular application. Such foam with an adhesive layer is available commercially from Avery Dennison of Painsville, Ohio. While not illustrated, the anchor pad 16 can include suture holes in addition to the adhesive layer to further secure the anchor pad to the patient's skin.

In other variations, a hydrocolloid adhesive or zinc oxide-based adhesive can advantageously be used upon the anchor pad 16 for attaching the anchor pad to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

A surface of the upper foam layer constitutes an upper surface 50 of the anchor pad 16. The upper surface 50 can be roughened by corona-treating the foam with a low electric charge. The roughened or porous upper surface can improve the quality of the adhesive joint (which is described below) with the bottom surface of the retainer 18.

A removable paper or plastic release liner 52 desirably covers the adhesive lower surface 34 before use. The liner 52 suitably resists tearing and desirably is divided into a plurality of pieces to ease attachment of the pad to a patient's skin.

The liner 52 comprises a folded over portion to define a pull tab 56. The pull tab 56 can be utilized to remove the paper or plastic release liner 52 from the adhesive lower surface 34 before use. A healthcare worker uses the pull tab 56 by grasping and pulling on it so that the liner 52 is separated from the lower surface 34. The pull tab 56 overcomes any requirement that the healthcare worker pick at a corner edge or other segment of the liner 52 in order to separate the liner 52 from the adhesive layer.

The pull tab 56 of course can be designed in a variety of configurations. For example, the pull tab 56 can be located along a center line of the anchor pad 16; or alternatively, the pull tab can be located along any line of the anchor pad 16 in order to ease the application of the anchor pad 16 onto the patient's skin at a specific site. For example, an area of a patient's skin with an abrupt bend, such as at a joint, can require that the pull tab 56 be aligned toward one of the lateral ends of the anchor pad 16 rather than along the center line. In the embodiment illustrated in FIG. 2, the fold forming the pull tab 56 is located along a centerline 54.

In another variation, the anchor pad 16 comprises a laminate structure with an upper woven layer and a lower adhesive layer. The upper layer can be polyester or other suitable polymer or textile materials. One particular suitable material is woven polyester available commercially under the name "Tricot" from Tyco. The lower adhesive layer constitutes the lower surface 34 of the anchor pad.

Retainer

Figure 3:
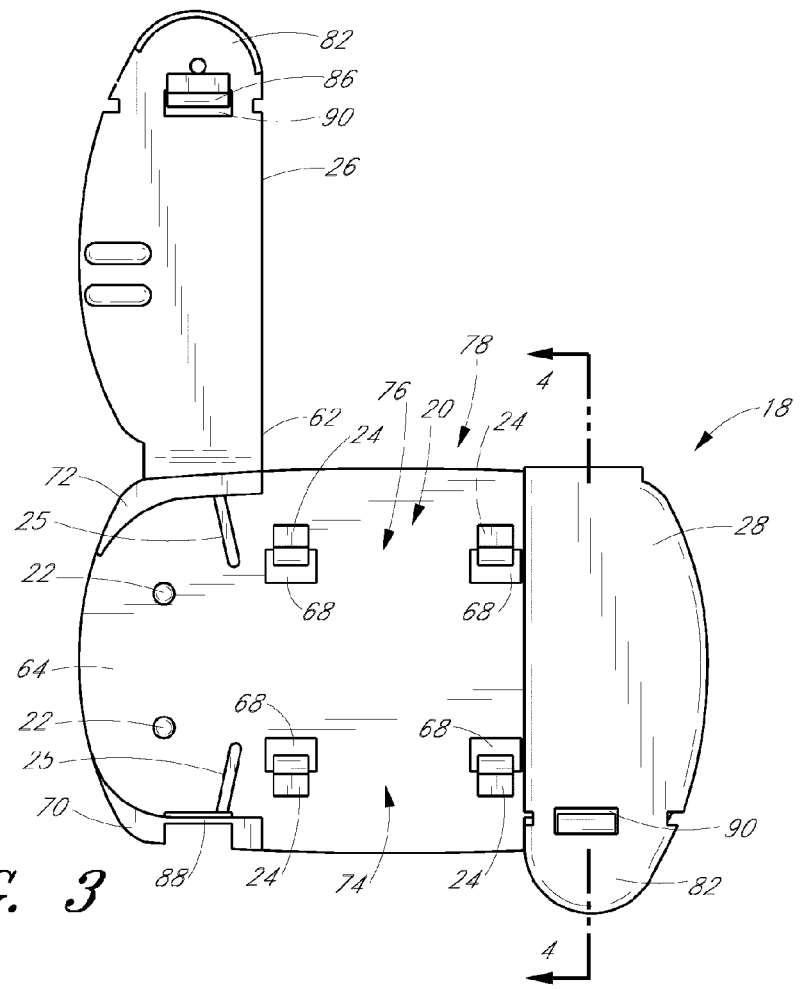
FIG. 3 is a top plan view of a retainer of the anchoring system of FIG. 1 shown with one cover in an open position and one cover in the closed position.
Figure 5:
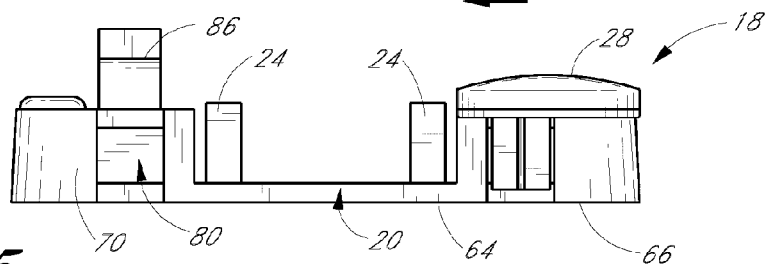
FIG. 5 is a front elevational view of the retainer of FIG. 3.
Figure 4:
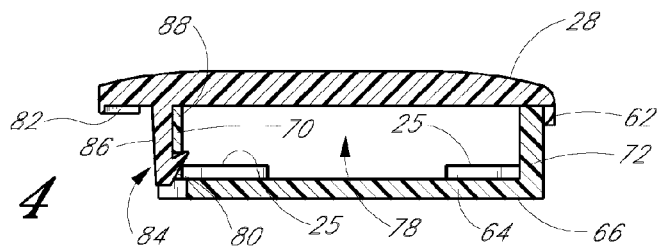
FIG. 4 is a cross-sectional view of the retainer of FIG. 3 taken along line 4-4.

With reference now to FIGS. 3-5, in one illustrated embodiment, the base 20 and the covers 26, 28 principally define the retainer 18. As noted above, the cover assembly comprises two covers 26, 28, each of which is connected to the base 20 by a folding hinge 62. This arrangement allows the base 20 and the covers 26, 28 to be formed as a unitary piece. Forming the base 20 and the covers 26, 28 in a unitary piece can be accomplished by any of a variety of ways well known to those skilled in the art. For instance, the base 20 and the cover assembly can be injection molded in order to reduce fabrication costs. In other embodiments, the retainer 18 may not have a cover assembly, or the covers 26, 28 may not be attached to or integrally manufactured with the base 20. In other embodiments, the retainer 18 comprises a single cover hinged to the base 20. The single cover may attach to the base 20 with a single hinge 62 or with multiple hinges. The single cover may further extend over portions of the fitting 30, 32 disposed on both sides of the longitudinal axis.

As will become apparent, several features of the cover assembly and base 20 are desirably flexible. Suitable materials which are both sufficiently strong, but flexible include without limitation: plastics, polymers, or composites such as polypropylene, polyethylene, polycarbonate, polyvinylchloride, acrylonitrile butadiene styrene, styrene butadiene, nylon, olefin, acrylic, polyester, moldable silicon, thermoplastic urethane, thermoplastic elastomers, thermoset plastics and the like. The retainer 18 is suitably formed by injection molding using a styrene butadiene polymer, such as KRO3 resin, available commercially from Phillips Petroleum of Houston, Tex. However, other materials can be used, and the retainer can comprise a multi-piece base 20 or cover 26, 28 as well.

In the embodiment illustrated in FIG. 3, the base 20 defines a receiving space having a hollow, generally rectangular shape. The base 20 can be configured in a variety of shapes, however, such as circular, square, or trapezoidal, in order to suit a particular application. For example, the base 20 may be configured to generally match the shape of the anchor pad 16 or the shape of the catheter fittings 30, 32. In the illustrated embodiment, a rectangular shape is preferably used to allow the base 20 and covers 26, 28 to be integrally formed and to capture both configurations of the catheter fittings 30, 32.

The longitudinal, lateral and transverse dimensions of the retainer 18 desirably are sized to stabilize the catheter 12, including its fittings 30, 32. In particular, the longitudinal dimension of the base 20 is preferably long enough to stabilize the retained length of the catheter 12. That is, the length of the catheter 12, which is secured within the retainer 18, is sufficient to inhibit rocking of the catheter 12 relative to the retainer 18. The longitudinal dimension of the base 20 should also be sufficient to receive the largest length of catheter fittings 30, 32 for which the retainer 18 is designed.

The lateral dimension of the base 20 is suitably sized to accommodate the largest width of catheter fittings 30, 32 for which the retainer 18 is designed. As with the longitudinal dimension, the lateral dimension may be sized to receive a single fitting 30, 32 or other portion of the catheter 12 without regard to the dimensions of the other fitting 30, 32. It is preferred that the lateral dimension be sufficient to provide the health care provider with a convenient and natural grip of the base 20 of the retainer 18 while allowing the healthcare worker to manipulate the covers 26, 28, posts 22 and/or clips 24 of the retainer 18. The lateral dimension also preferably provides sufficient width to mount hinges and latch mechanisms in the present embodiment, as described below.

The transverse height of the base 20 preferably corresponds generally to the thickest catheter fitting for which the retainer 18 is designed. While the catheter body or central portion of the fitting may have a greater thickness than the fitting's wing thickness, the base 20 accommodates this through its open central region between the covers 26, 28. The base 20 thus need not have a greater transverse height than that of the catheter 12, and consequently, the overall profile of the retainer 18 can be minimized.

As understood from FIGS. 3-5, a bottom wall 64 of the base 20 includes a substantially flat bottom surface 66, preferably with recesses 68 that extend upward through the bottom wall 64. The recesses 68 extend transversely from the lower side of the bottom wall 64 to the upper side of the bottom wall 64, and have lateral and longitudinal widths sufficient to provide a degree of flex to the clips 24 that are disposed on the base 20. As a result of these recesses 68, less of the relatively stiff material that makes up the base 20 needs to flex in order to engage and disengage the second fitting 32. The retainer 18, however, need not include the recesses 68 in all embodiments.

Additionally, in other embodiments, the bottom surface 66 of the base 20 need not be perfectly flat, and may include contouring in order to assist in stabilizing the retainer 18 when placed on the skin of a patient. The bottom surface 66 may, for example, have a concave curved shape when viewed from the front along a longitudinal axis. The amount and radius of curvature may be varied depending on the expected location of usage or application of the securement device 16. Such a curved profile of the bottom surface 66 allows for a closer match between the contour of the bottom of the base 20 and the shape of the body of the patient. It will be appreciated that many common sites for insertion of medical lines which require securement will be located on anatomical regions exhibiting convex curvature, such as the arms, legs, shoulders, etc. By providing a concave bottom profile to the base 20 of the retainer 18, the retainer will rock less once placed upon the patient via the anchor pad 14. This will help prevent the retainer from pulling free from the anchor pad along the lateral edges of the base 20, and also inhibits undesirable rotation of the retainer 18 due to the bottom surface 66 rolling along the body of the patient. For example, the curvature of the base 20 can be sized to generally match the curvature on a dorsal side of an average patient's hand for certain applications.

While not shown in the illustrated embodiment, the bottom surface 66 may also be angled in the longitudinal direction. This angle is used in order to align the axis of the retainer 18 with the desired incident angle with which the catheter 12 is to contact the skin of the patient. A variety of different angles may be used, ranging from 0° to 45°, and more suitably from 5° to 25°. For instance, for the securement of arterial catheters, it is desirable for the angle of incidence of the catheter to the skin of the patient to be about 12.5°. For the securement of intravenous catheters, it is desirable for the angle of incidence of the catheter to the skin of the patient to be about 7° to 15°. By angling the bottom surface 66 of the base 20 at the desired angle, which will depend upon the particular securement application (e.g., securing an arterial catheter, an intravenous catheter, etc.), the proper angle of incidence for a catheter can be maintained.

The interior of the base 20 need not be completely solid. Indentations and other empty regions or voids may be included on the base 20 for a variety of reasons. For instance, certain indentations required by the manufacturing process may be located on the bottom wall 64 of the base 20 in order to avoid exposing these indentations during use of the retainer 18. Those of skill in the art will recognize that these indentations or other incongruities need not be used, but may be included in certain applications for reasons including but not limited to, lightening of the overall retainer structure, adding flexibility to the retainer and or clips 24, or providing a more advantageous surface for attachment between the base 20 and the anchor pad 14.

In one embodiment, the retainer 18 includes at least one post 22 disposed on the base 20. In the embodiment illustrated in FIGS. 1-8, the base 20 includes four posts 22, one for each opening 40 formed in the first fitting 30 to provide greater security in the engagement. Each opening 40 in the first fitting 30 corresponds to a post 22, such that the corresponding post 22 protrudes from the bottom wall 64 of the base 20 through an opening 40 when the catheter 12 is in the first inserted position. In other embodiments, the anchoring system 10 may include more or less than four post-opening pairings, as will be understood by one of ordinary skill in the art.

In order to aid the manufacture and assembly of the retainer 18, the posts 22 may be formed as part of the base 20. They may also be constructed in a number of different ways well known to those of skill in the art, and may have a variety of different configurations such as, for example, include tapering cross-sections.

The posts 22 suitably are formed to have a circular cross-section with a slightly smaller diameter than the diameter of the openings 40, although other shapes and cross-sections are possible. In another embodiment, the posts 22 may have flanges or other radial projections disposed on their upper ends (i.e., the ends farthest from the base bottom wall 64). These projections further help to secure the catheter 12 to the retainer 18. In the preferred embodiment, the posts 22 have a large enough diameter to provide stiffness, as well as to minimize longitudinal or lateral movement between the openings 40 and the posts 22.

In one embodiment, the retainer 18 also includes at least two clip 24 disposed on the base 20. In the illustrated embodiment, the base 20 includes four clips 24 configured to surround the perimeter of the second fitting 32 when the catheter 12 is in the second inserted position. The four clips 24 are arranged on the base so as not to interfere with the first fitting 30 when the catheter is in the first inserted position. Other numbers and arrangements of clips 24 are, of course, possible. In one embodiment, only one clip 24 is employed. In order to provide securement using one clip 24, some further retainer mechanism should be employed in combination with the clip. For example, the fitting may be secured between one clip and a sidewall of the base 20 or an adhesive may be employed between the fitting 30, 32 and the retainer 18. In other embodiments, two, three or more clips may be employed, often in combination with a friction fitting with a sidewall of the base 20 or with corresponding structure (e.g., a notch) on the fitting 30, 32.

The clips 24 in accordance with one embodiment comprise a transverse extending rectangular section, with a tang disposed at its upper end (i.e., an end farthest from the base bottom wall 64). The clips 24 are preferably formed such that the rectangular section has a height greater than the transverse height of the second fitting 32. In this manner, the second fitting 32 can fit between the tangs of the clips 24 and the upper surface of the bottom wall 64 of the base 20.

In the illustrated embodiment, as the second fitting 32 is moved into the second inserted position, the clips 24 will flex as the tangs move past the wing portions 44 of the second fitting 32, and then will relax or spring back at least generally to their original state once the tangs have moved past the second fitting 32 to a position above but preferably close to the top of the second fitting 32. This will prevent the second fitting 32 from unintentionally moving out of the second inserted position. The rectangular housing 48 of the second fitting 32 also preferably serves to limit lateral movement between the clips 24 and the second fitting 32. The second fitting 32 suitably has a complementary shape to that of the bottom of the tangs to promote engagement between them when the second fitting 32 is disposed within the retainer 18. In the illustrated embodiment, the top of the second fitting 32 is generally normal to the transverse axis in the same manner as the bottom of the tangs of the clips 24.

Although the embodiments shown employ clips or posts, it should be understood that other retainer mechanisms for providing attachment between the medical line 12 and the securement device 16 may also be used. In one embodiment, clips in a variety of locations and configurations may be used, such that some clips are configured to engage some fittings and other clips are configured to engage other fittings. In another embodiment, only posts are used in a variety of locations and configurations. In yet another embodiment, other retainer mechanisms, including for example chemical engagement means (e.g. adhesive), may be used in combination with other retainer mechanisms to provide a single or dual-securement anchoring system.

As best seen in FIGS. 3-5, the base 20 includes upstanding front and back walls 70, 72 that are spaced apart in the longitudinal direction, and extend upward from the bottom wall 64 of the base 20. Openings 74, 76 generally bifurcate each wall 70, 72, respectively, to allow the catheter 12 to pass through one wall 70, through the receiving space 78, above the lower wall 64 of the base 20, and then out the opposite wall 72. As is best seen in FIG. 5, other openings 80 are also formed in the front walls 70 in order to facilitate engagement with the latching mechanism disposed on the covers 26, 28, as will be described in further detail below. In other embodiments, the front and back walls 70, 72 may be formed in other configurations.

In the illustrated embodiment, there are no sidewalls formed on the lateral portions of the base 20. In other embodiments, such walls may be employed. The receiving space 78 is formed on the base 20 between the lateral edges of the base 20. The receiving space 78 is desirably formed so as to accept and retain a portion of the catheter 12 or one of the catheter fittings 30, 32, and in particular the wings thereof, without occluding the lumen of the catheter 12.

As seen in FIGS. 3 and 4, each of the covers 26, 28 has a size and shape that desirably is approximately coextensive with the longitudinal dimension of the base 20. Although each cover 26, 28 extends longitudinally at least as far as the base 20 does, the covers 26, 28 need not span the entire lateral dimension of the base. This will be discussed below. In some embodiments and applications, it is desirable for the covers 26, 28 to be larger longitudinally than the base 20. By protruding beyond the longitudinal dimension of the base 20, the covers 26, 28 can also include flanges 82 that are useful in operation of the latch mechanisms. In other modes, the covers 26, 28 need not include the flanges 82.

Each cover 26, 28 suitably is connected to the base 20 by at least one hinge 62 to provide each cover 26, 28 with at least two positions: an open position, in which the receiving space 78 of the base 20 is exposed and into which a catheter 12 and/or one of the fittings 30, 32 may be inserted; and a closed position, in which the cover is located over the base 20 and covers at least a portion of the receiving space 78. In the closed position, each of the covers 26, 28 is held in place by a corresponding latch mechanism, described below, to inhibit the unintentional transverse release of the catheter 12 or one of the catheter fittings 30, 32 from the receiving space 78 of the base 20. In a preferred embodiment, the covers 26, 28 are sufficiently sized to accommodate the necessary latch mechanism components and to extend over or around at least a portion of the posts 22 (and possibly receive upper ends of the posts) when in the closed position. Though not shown, in one embodiment, the interaction between upper portions of the posts 22 and the covers 26, 28 when the covers 26, 28 are in the closed position inhibits movement or play of the post upper ends relative to the covers 26, 28. Consequently, this interaction may inhibit the posts 22 from deflecting or bending, at least in the longitudinal direction, when the catheter 12 is tugged, thereby maintaining a secure connection between the posts 22 and the catheter 12.

The hinges 62 need not provide 180° of movement for the covers 26, 28 relative to the base 20 to establish a closed position and a fully open position. For instance, the hinges 62 can permit a smaller degree of movement (e.g., 90°) between the base 20 and the covers 26, 28 while still providing enough space to transversely insert the fitting 30, 32 or catheter 12 into the retainer 18 when both covers 26, 28 are open.

Figure 6:
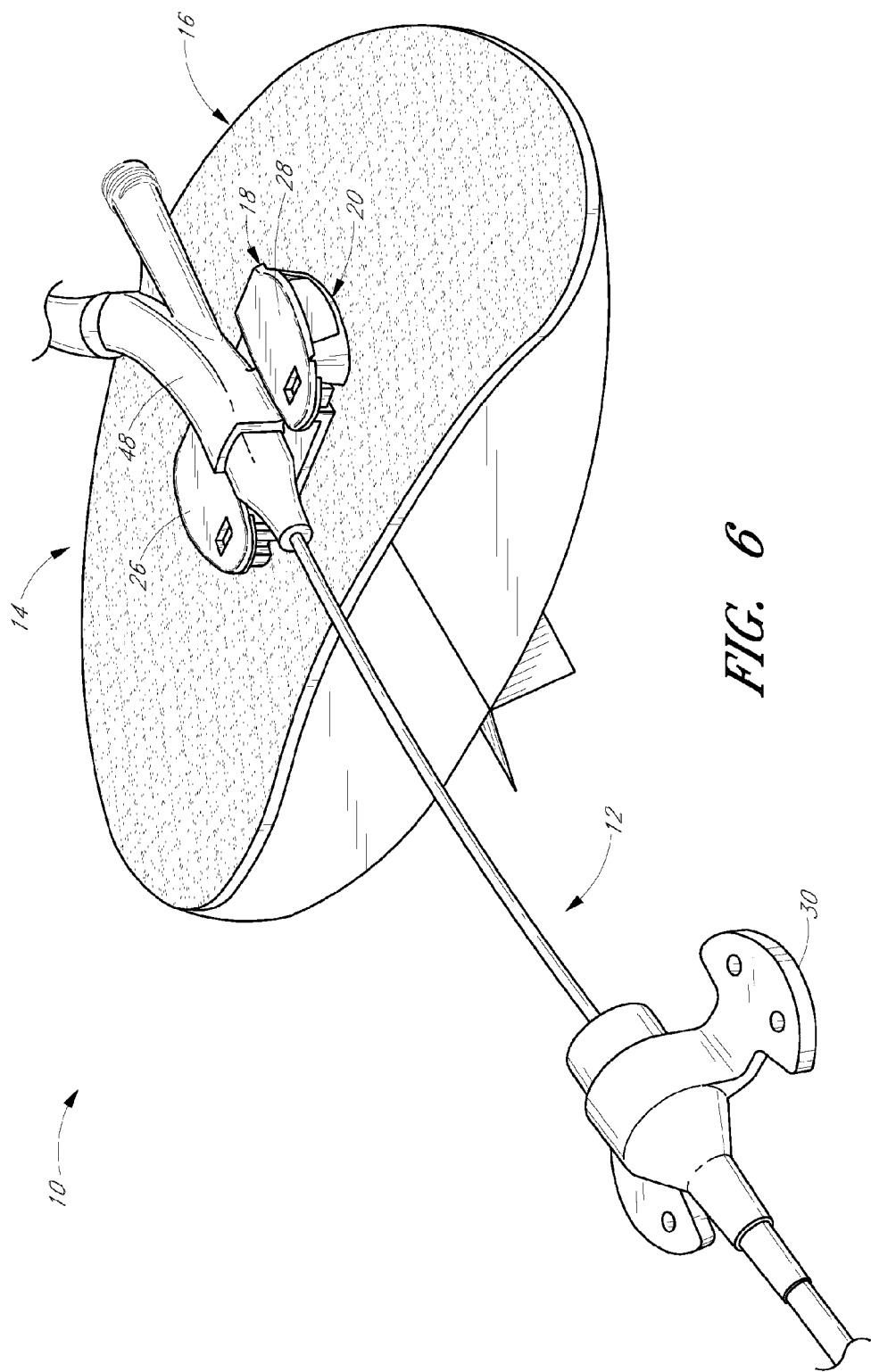
FIG. 6 is a perspective view of the medical article anchoring system of FIG. 1 with the medical article in a second inserted position, shown with both covers of the retainer in the closed position.
Figure 7:
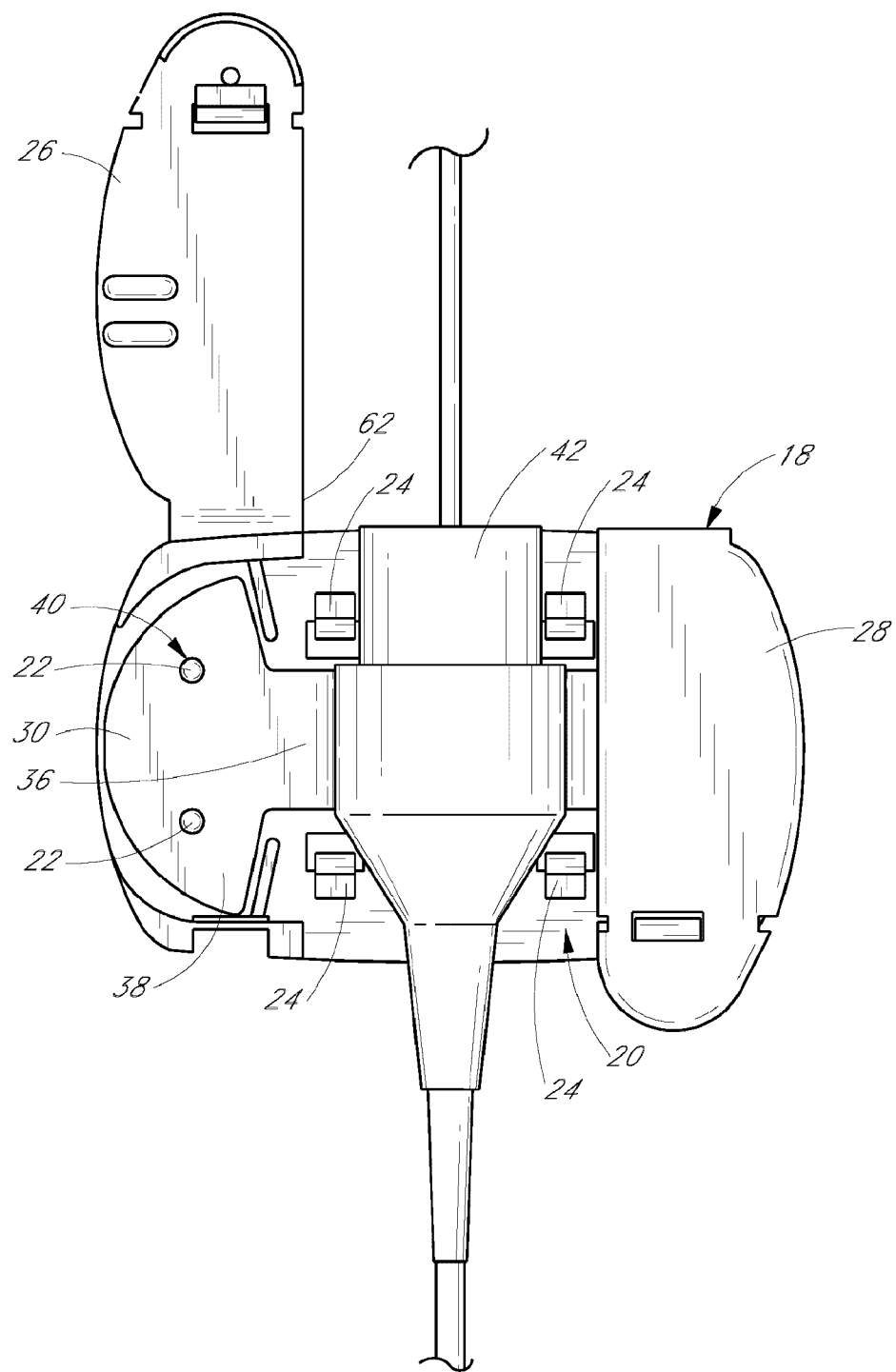
FIG. 7 is a top plan view of the medical article of FIG. 1 in the first inserted position in the retainer, shown with one cover in the open position and one cover in the closed position.
Figure 8:
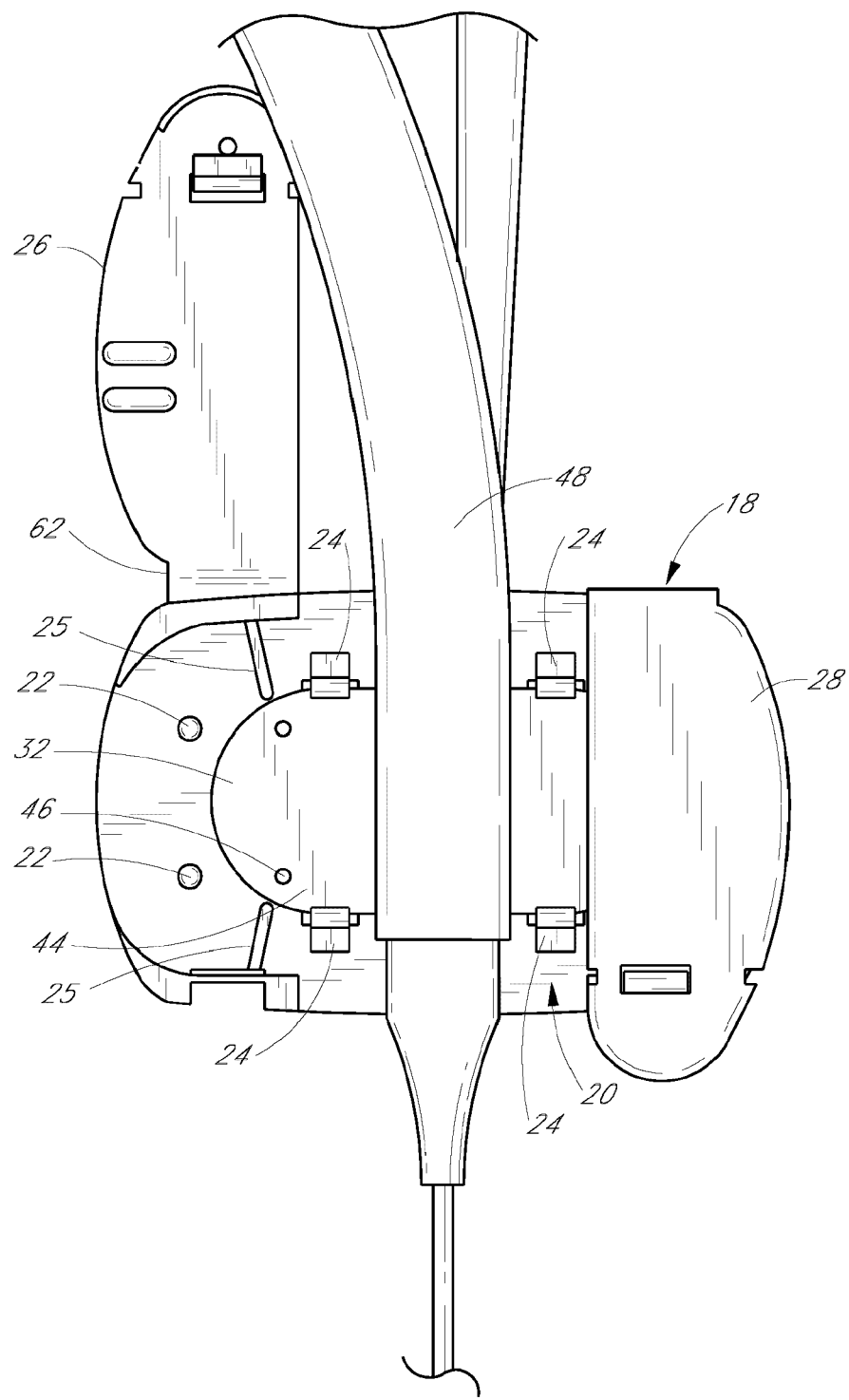
FIG. 8 is a top plan view of the medical article of FIG. 1 in a second inserted position in the retainer, shown with one cover in the open position and one cover in the closed position.

In the embodiment shown in FIGS. 3-5, each cover 26, 28 of the cover assembly has a hinge 62 and a latch mechanism, such that each cover can be independently placed into an open or a closed position. In this embodiment, the covers 26, 28 do not contact one another when both are in the closed position, as shown in FIGS. 1 and 6. Since both covers 26, 28 do not cover the entire lateral dimension of the retainer 18, it becomes possible to effectively secure catheters or fittings that extend transversely beyond the height which could not be contained below the covers if the covers were to meet. By allowing such "centrally bulky" catheters or fittings to be accepted, the anchoring system 10 is more universal and has a lower profile as noted above. An example of how the retainer 18 and posts 22 hold a "centrally bulky" catheter 12 is shown in FIGS. 1 and 7, while an example of how the retainer 18 and clips 24 hold such a catheter 12 is shown in FIGS. 6 and 8.

As can be seen in FIG. 3, each hinge 62 in the illustrated embodiment comprises a flexible section of material that can take any number of forms to mechanically connect the covers 26, 28 to the base 20 while permitting pivotal movement of the covers 26, 28 relative to the base 20 so as to enable engagement or disengagement of these parts, as described below. In the illustrated embodiment, the band is formed of the same material from which the base 20 and covers 26, 28 are comprised. Advantageously, the hinges 62 are integrally molded with the base 20 and the covers 26, 28 to form a unitary member, as noted above. The hinges 62 are attached to the back wall 72 of the base 20; however, the hinges 62 need not open and close in the longitudinal direction as illustrated. In other embodiments, the covers 26, 28 may be laterally or otherwise disposed.

As best understood from FIG. 3, the width of the hinges 62, as measured in the lateral direction, is desirably less than that of either the base 20 or the covers 26, 28 to allow some leeway or play when engaging or disengaging the covers 26, 28 to or from the base 20. That is, this shape allows the hinge 62 to twist to some degree to compensate for some manufacturing tolerances; however, the hinges 62 can have at least as large of a lateral dimension as the base 20 and/or the covers 26, 28.

As discussed above and illustrated in FIG. 4, a latch mechanism 84 is provided for securing the covers 26, 28 in the closed position relative to the base 20. In one embodiment, the latch mechanism 84 comprises at least one cover clip 86 and at least one latch 88. In the illustrated embodiment of FIG. 4, the cover clip 86 is disposed on the cover 26 while the latch 88 is disposed on the base 20. However, those skilled in the art will recognize that the cover clip can be disposed on the base and the latch can be disposed on the cover.

Each cover clip 86 extends from the cover 26 toward the base 20 of the retainer 18 from the lower side of the cover 26 ("lower" as seen when the cover 26 is in the closed position as in FIG. 4). In addition to extending from the cover 26, each cover clip 86 has at the free-end a tang that extends in the direction toward the corresponding latch 88 and receiving space 78. The tang illustrated in FIG. 4 has a surface that lies generally normal (e.g., ±15° from perpendicular) to the transverse axis; however, the tang can also be fairly rounded. The cover clip 86 is further characterized by its location near the opening 90 formed in the cover 26. By positioning the cover clip 86 at such a location, it has greater flex in the longitudinal direction. The greater flex is due to the hole 90 reducing the resistance of the cover 26 in that region to deformation.

As shown most clearly in FIG. 4, the latch 88 comprises a strip of material disposed above the opening 80 formed in the front wall 70 of the base 20, at a location configured to interact with the tang of the cover clip 86 when the cover 26 is in the closed position. In this closed position at least a portion of the tang of the cover clip 86 extends into the opening 80 and is inhibited from moving in a transverse direction by the latch 88.

As the cover 26 is moved into the closed position, the cover clip 86 will flex as the tang moves past the latch 88, and then will relax or spring back into its original state once the tang has moved past the latch 88 to a position adjacent the opening 80. This will prevent the cover 26 from unintentionally moving out of the closed position. The bottom of the latch 88 suitably has a complimentary shape to that of the top of the tang to promote engagement between them when the cover 26 is closed. In the illustrated embodiment, the bottom of the latch 88 is generally normal to the transverse axis in the same manner as the tang of the cover clip 86.

In order to allow disengagement of the latching mechanism 84, a healthcare worker flexes the cover clip 86 in a direction moving the tang away from the opening 80. With the tang disengaged from the opening 80, the cover 26 may be freely moved to the open position. In one mode of operation, this can be accomplished by pulling upon the flange 82 or other extension of the cover 26. By pulling up on the flange 82 in a transverse direction, the cover 26 bends, moving the tang of the cover clip 86 away from the latch 88, and allowing the cover 26 to be moved out of the closed position without exerting excessive force upon the cover 26. The opening 90 in the cover 26 aids in allowing the cover 26 to bend in this manner.

In the illustrated embodiment, each cover 26, 28 has one cover clip 86 with a corresponding latch 88 on the base 20. The latch mechanisms 80 on each cover 26, 28 can be formed as mirror images of each other. In other embodiments, other latching mechanisms may be employed, as is well known to those of skill in the art.

After the retainer 18 is manufactured, it is attached to the upper surface 50 of the anchor pad 14. The base 20 desirably is secured to the upper surface 50 by a solvent bond adhesive, cyanoacrylate or other bonding material. One such adhesive is available commercially as Part No. 4693 from the Minnesota Mining and Manufacturing Company (3M). With certain types of polymer (e.g., a styrene butadiene polymer), a UV cured adhesive also can be used, as known in the art. Of course, other methods of securing the retainer 18 to the anchor pad 14 may also be used, including mechanical methods such as sewing or stapling the two together.

When the anchoring system 10 is assembled as described above, the receiving space 78 formed between the base 20 and covers 26, 28 when they are in the closed position defines a channel. The channel is capable of receiving a portion or length of the catheter 12 and is generally configured to house, grip and secure the affected catheter portion. In the illustrated embodiment, the channel has a generally symmetrical shape. However, other cross-sectional shapes may be used for particular applications, such as for supporting a Y-site catheter.

Although the shape of the channel may vary depending upon its application (i.e., depending upon a shape of the retained portion of the medical article for which the retainer is designed to be used), the length of the channel, as mentioned above, is desirably sufficient in the longitudinal direction to stabilize the catheter 12, rather than acting as a fulcrum for the catheter, as was discussed above. That is, the retainer 18 receives a sufficient length of the catheter to inhibit movement of the catheter 12 in the longitudinal and transverse directions, and preferably also in the lateral direction (i.e., to inhibit yaw, pitch and axial movement of the catheter), without kinking the catheter.

Other Embodiments

FIG. 9 is a perspective view of another embodiment of a medical article anchoring system that is configured in accordance with some of the aspects and features of the present invention described herein. The anchoring system shown in FIG. 9 includes an anchor pad and a retainer that are similar to the anchor pad and retainer described above, save the omission of the covers, posts and walls from the retainer and the way the catheter fitting attaches to the retainer. Accordingly, throughout the remainder of the detailed description like elements between the illustrated embodiments are referenced with like numerals with an "a" suffix designating the embodiment illustrated in FIGS. 9 through 12. Additionally, the detailed description of the elements of the anchoring system described above applies equally to the similar elements of the anchoring system illustrated in FIGS. 9 through 12, unless noted otherwise.

Figure 10:
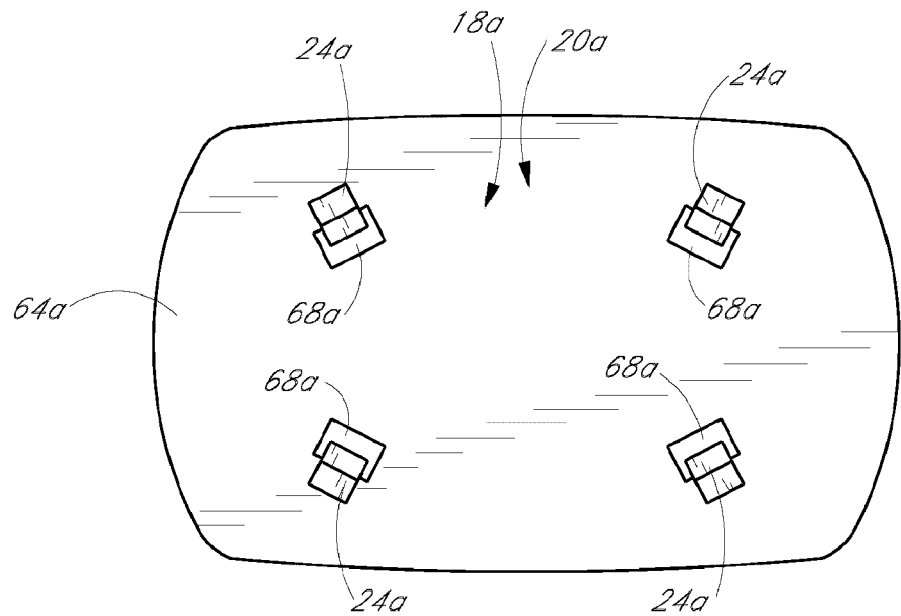
FIG. 10 is a top plan view of a retainer of the anchoring system of FIG. 9 shown with a plurality of clips.

With reference to FIGS. 9 and 10, the anchoring system 10a comprises a medical device, such as a catheter 12a, and a securement device 14a. The securement device 14a further comprises an anchor pad 16a, upon which rests a retainer 18a.

The anchor pad 16a illustrated in FIG. 9 is the same anchor pad 16 illustrated in FIG. 2 and accordingly the description of the anchor pad 16 of FIG. 2 applies equally to the anchor pad 16a illustrated in FIG. 9.

In the embodiment illustrated in FIG. 9, the section of catheter fitting 32a attaches to the retainer 18a via four clips 24a, although more or few clips can also be used as described above. The retainer 18a of the present embodiment and the retainer 18 illustrated in FIG. 2 both include one or more clips 24 for inhibiting a catheter 12 or fitting from moving in the longitudinal and transverse directions. As explained above, longitudinal and transverse movement is generally arrested by the holding effect provided by the clip(s) 24 of the retainer 18 illustrated in FIG. 2. This holding effect may also arrest lateral movement. The plurality of clips 24a of the retainer 18a are further disposed on the base 20a so as to further inhibit movement of the catheter 12a or fitting 32a in the lateral direction and to provide the same holding effect as the clips 24a of the retainer 18a.

The plurality of clips 24a extend upwardly from the base 20a. In the illustrated embodiment, the base 20a includes four clips 24a configured to surround the perimeter of the second fitting 32a of the catheter 12a. Other arrangements of clips 24a are possible.

While not included in the illustrated embodiments, the clips can be configured and positioned to interact and engage with corresponding structure on the fitting 32a to arrest at least some degree of movement of the fitting 32a relative to the retainer 18a using few clips. For example, the wings 44a of the fitting 32a can include notches at their lateral extremes, which have substantially the same longitudinal width of the clips 24a. When engaged, the clips 24a can fit into the notches with the clips preferably directly opposing each other. The clips 24a can hold wings 44a to the base 20a to inhibit transverse movement of the fitting 32a, and the interaction (or interengagement) between the clips 24a and the notches can inhibit longitudinal and/or lateral movement of the fitting 32a. The clips 24a in this embodiment can have a sufficient longitudinal width to stabilize further the fitting 32a on the retainer base 20a.

Additional retention features may be employed with the retainer 18a to further inhibit movement or provide redundant securement of the retained medical article. For example, the retainer 18a may employ one or more posts (similar to posts 22 described above) in addition to the one or more clips 24a. The one or more posts can be disposed on the base 20a of the retainer 18a so as to facilitate securement of more than one medical article or multiple portions of the same medical article having different shapes or sizes. Alternatively, the one or more of the posts and one or more of the clips 24a may together inhibit movement of a single medical article or a single portion of the medical article. For example, but without limitation, a retainer can include two clips 24a and one post to inhibit longitudinal, lateral and/or transverse movement of the retained section of the medical article relative to the retainer.

In the embodiment illustrated in FIG. 9, the base 20a of the retainer 18a supports the four clips 24a. The four clips 24a are disposed on the base 20a so as to accept, to retain and to secure a section of the catheter fitting 32a. Of course the four clips 24a may be disposed on the base 20a in a multitude of locations as well as being spaced apart from one another depending on the geometry of the catheter fitting 32a to be retained.

Figure 11:
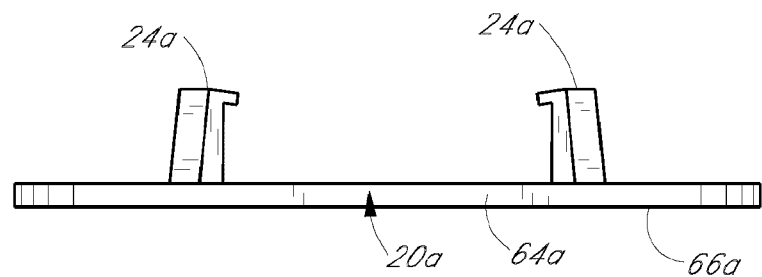
FIG. 11 is a front elevational view of the retainer of FIG. 10.

As understood from FIGS. 10 and 11, a bottom wall 64a of the base 20a includes a substantially flat bottom or lower surface 66a, with recesses 68a that extend upward through the bottom wall 64a. In other embodiments, the bottom surface 66a of the base 20a is not perfectly flat, and may include contouring in order to assist in stabilizing the retainer 18a when placed on the skin of a patient.

These recesses 68a extend transversely from the lower side of the bottom wall 64a to the upper side of the bottom wall 64a, and have lateral and longitudinal widths sufficient to provide a degree of flex to the clips 24a that also comprise a portion of the base 20a. As a result of these recesses 68a, less of the relatively stiff material that makes up the base 20a needs to flex in order to engage and disengage the second fitting 32a. The other variants of the base described above can also be practiced with this embodiment.

FIG. 11 is a front view of the retainer 18a of FIG. 10. In the illustrated embodiment, the base 20a principally defines the retainer 18a and need not have a cover assembly. The interior of the base 20a need not be completely solid. Indentations and other empty regions or voids may be included on the base 20a for a variety of reasons.

Each clip 24a in accordance with one embodiment comprises a transversely extending rectangular section with a tang disposed at its upper end. The clips 24a are suitably formed such that the rectangular section has a height greater (and preferably only slightly greater) than the transverse height of the second fitting 32a and such that the second fitting 3a2 can fit between the lower surfaces of the tangs of the clips 24a and the upper surface of the bottom wall 64a of the base 20a.

In the illustrated embodiment, as the second fitting 32a is moved into position, the clips 24a will flex as the tangs move past the wing portions 44a of the second fitting 32a, and then will relax or spring back to their original state once the tangs have moved past the second fitting 32a to a position above but preferably close to the top of the second fitting 32a. This will inhibit the second fitting 32a from unintentionally moving out of the inserted position and inhibits transverse movement between the clips 24a and the second fitting 32a.

In the illustrated embodiment, the four clips are arranged on the receiving area of the base 20a so as to generally face the fitting 32a. Two of the four clips 24a are arranged on each side of a longitudinal axis that bisects the receiving area on the base 20a. Each such pair of clips 24a preferably is arranged on a line that lies at least substantially parallel with the longitudinal axis. Additionally, the two proximate-most clips 24a preferably are arranged on a first line that lies at least substantially perpendicular to the longitudinal axis, and the two distal-most clips 24a preferably are arranged on a second line that lies at least substantially parallel to the first line and at least substantially perpendicular to the longitudinal axis. This symmetric orientation of clips 24a about the fitting 32a reduces the number of clips 24a without meaningfully reducing the retaining effect provided by the clips 24a.

By angling the clips 24a relative to the lateral and longitudinal directions, the clips 24a serve to inhibit lateral and longitudinal movement between the clips 24a and the second fitting 32a. While all four clips 24a are angled in the illustrated embodiment, lateral and longitudinal movement may be arrested with two angled clips 24 on opposite lateral sides of the second fitting 32a or catheter 12a. The second fitting 32a suitably has a complementary shape to that of the bottom of the tangs to promote engagement between them when the catheter 12a is inserted. In the illustrated embodiment, the top of the second fitting 32a is suitably generally normal to the transverse axis in the same manner as the bottom of the tangs of the clips 24a.

In general, the plurality of clips 24a of the retainer 18a preferably is arranged on the receiving area of the base 20a so as to inhibit movement of the fitting in the longitudinal and transverse directions (and preferably also in the lateral direction) relative to the securement device. At least some of the clips 24a clips are arranged on the receiving area so as to abut the laterally extending surfaces, and preferably both the laterally and longitudinally extending surfaces of the fitting to thereby inhibit movement of the fitting in the longitudinal and lateral directions relative to the securement device. In the illustrated embodiment, which includes four clips 24a, the clips 24a are arranged on the receiving area in two sets, each set facing generally towards the other set.

FIG. 12 is an enlarged top plan view of the medical article 12a of FIG. 9 inserted in the retainer 18a and retained by the plurality of clips 24a. As shown in FIGS. 9 and 12, the second fitting 32a can be positioned over the retainer 18a such that the clips 24a are aligned with the perimeter of the second fitting 32a. The second fitting 32a can then be pressed into the retainer 18a, such that the clips 24a initially flex away from the second fitting 32a and then spring back around the second fitting 32a once the second fitting 32a passes by the tangs.

If the catheter 12a is pulled in an upward, transverse direction, the holding effect of one or more tangs of the clips 24a prevents the catheter 12a from disengaging from the retainer 18a. The retainer 18a thus inhibits transverse movement of the catheter 12a relative to the retainer 18a. By angling two or more of the clips 24a relative to the longitudinal and transverse directions, the clips 24a restricts movement of the catheter 12a in the transverse and lateral directions.

Longitudinal and lateral movement may be inhibited by only two angled clips 24a. For example, two of the four clips 24a may be arranged on the base 20a so as to abut both lateral and longitudinal surfaces of the catheter 12a to thereby inhibit movement of the catheter 12a in the longitudinal and lateral directions. One or more of the two angled clips 24a or one or more of the remaining two clips 24a may include a tang portion for inhibiting transverse movement. For example, the tang portion may be spaced from the base by a sufficient distance to accommodate at least a portion of the catheter 12a between the base 20a and the tang portion so as to thereby inhibit movement of the catheter 12a in the transverse direction.

Operation

In operation, as best seen in FIGS. 2 and 9, the healthcare worker can easily secure a catheter 12, 12a (or other medical article) to a patient using the above-described securement devices 14, 14a or a readily apparent modification thereof. In the illustrated embodiment, the healthcare worker first determines the most desirable insertion sites for the catheter 12, 12a and attachment sites for the securement device 14, 14a, and thereby determines what the distance between these sites is likely to be. The clips 24a of the embodiment illustrated in FIG. 9 are disposed so as to receive and secure a catheter 12a or other medical article between the clips 24a. The multiple retention features of the securement device 14 of the embodiment illustrated in FIG. 2 receive and secure a catheter 12 or other medical article at multiple locations, for example, first and second fittings 30, 32, along the body of the catheter 12.

For the embodiment of the securement device 14 illustrated in FIG. 2, the practitioner can then choose the first or the second fitting 30, 32 to determine the distance that the catheter 12 will extend forward from the securement device 14 towards the insertion site. As illustrated in FIG. 1, use of the first fitting 30 minimizes the distance between the insertion and attachment sites, while, as illustrated in FIG. 6, use of the second fitting 32 maximizes this distance. The healthcare provider also can use two identical securement devices 14 to secure both fittings 30, 32 on the patient to provide multiple securement points along the length of the catheter 12. In other embodiments, the medical practitioner may be able to choose among different catheters with different fittings disposed at varying locations along their lengths depending on the desired distance between the insertion and attachment sites. In still other embodiments, the practitioner may not make this initial choice, but the securement device 14 may facilitate the use of different catheters and fittings with the same securement device. While not illustrated in FIGS. 2 and 9, the practitioner may engage a catheter with the securement device using clips disposed on the fitting or a combination of clips disposed on both the fitting and the securement device.

In one application, shown nearly completed in FIG. 7, the medical practitioner first opens the covers 26, 28 of the retainer 18 to expose the base 20. With the retainer 18 in the open position, the first fitting 30 can be aligned over the retainer 18 such that the posts 22 are aligned with the openings 40 in the first fitting 30. The first fitting 30 can then be pressed into the retainer 18. Significantly, the narrow connecting portion 36 of the first fitting 30 does not engage the clips 24. Thus, the retainer 18 can provide differing means of attachment for the two fittings 30, 32. The wing portions 38 flare out from this narrow connecting portion 36 to engage the posts 22, and further to be at least partially disposed beneath the covers 26, 28 in the closed position.

In another application, shown in FIG. 8, the medical practitioner first opens the covers 26, 28 of the retainer 18 to expose the base 20. With the retainer 18 in the open position, the second fitting 32 can be positioned over the retainer 18 such that the clips 24 are aligned with the perimeter of the second fitting 32. The second fitting 32 can then be pressed into the retainer 18, such that the clips 24 flex and spring back around the second fitting 32. Significantly, the second fitting 32 is narrower in the lateral direction than the first fitting 30, and so does not engage or interfere with the posts 22. In a preferred embodiment, the second fitting 32 does have sufficient lateral width to be at least partially disposed beneath the covers 26, 28 in the closed position. The walls 25 are disposed on the base 20 and inhibit lateral movement of the fitting 32.

In another application, shown in FIG. 12, the medical practitioner positions the second fitting 32a over the retainer 18a such that the clips 24a are aligned with the perimeter of the second fitting 32a. The second fitting 32a can then be pressed into the retainer 18a, such that the clips 24a flex and spring back around the second fitting 32a. By angling the clips 24a relative to the lateral and longitudinal directions, the clips 24a serve to inhibit lateral and longitudinal movement between the clips 24a and the second fitting 32a.

As illustrated in FIGS. 7 and 8, once one of the fittings 30, 32 is inserted within the retainer 18, the covers 26, 28 are moved towards their closed positions. In FIGS. 7 and 8, the cover 26 is shown still in the open position, while the other cover 28 has been closed. The relatively thin strip of material forming the hinge 62 allows the hinge to bend when finger pressure is exerted on the covers 26, 28 to close them. The tangs of the cover clips 86 contact the latches 88 on the base 20 when the covers 26, 28 near their closed position. Continued pressure forces the cover clips 86 outward to permit the tangs of the cover clips 86 to pass beyond the latches 88. The tangs of the cover clips 86 snap over the latches 88, and project into at least a portion of the openings 80 in the base 20 under the spring force provided by the deflected cover clips 86 when the covers 26, 28 are in the closed position. The interaction between the tangs of the cover clips 86 and the corresponding lower surfaces of the latches 88 hold the covers 26, 28 in this position.

To open the latch mechanism 84, the healthcare worker pull upwards on the protruding flanges 82 of the covers 26, 28, as described above. The resulting outwardly directed force deflects the cover clips 86 to clear the latches 88. The healthcare worker can then remove either of the fittings 30, 32 from the retainer 18.

The releasable engagements between the covers 26, 28, fittings 30, 32 and the base 20 allow the same retainer 18 to be used for an extended period of time, while permitting repeated attachment and reattachment of the catheter 12 or fittings 30, 32 to and from the securement device 14. In addition, the hinges 62 which connect the covers 26, 28 to the base 20 ensure that the covers will not be lost or misplaced when the catheter 12 is detached from the securement device 14. The healthcare worker wastes no time in searching for a misplaced cover, or in orienting a cover prior to latching, and he or she is not required to carry a separate instrument to detach the catheter 12 from the securement device 14.

If the catheter 12 is pulled in the longitudinal direction, the holding effect of the posts 22 and openings 40, or clips 24 prevent the catheter 12 from pulling through the retainer 18. The retainer 18 thus inhibits longitudinal movement of the catheter 12 relative to the retainer. Interaction between the base 20, covers 26, 28, posts 22 and holes 40 and/or clips 24 and rectangular housing 48 restrict movement of the catheter 12 in the transverse and lateral directions.

Importantly, the base 20 and covers 26, 28 do not crimp or kink the catheter body and occlude the lumen(s) therein when it is inserted within the retainer 18.

The retainer 18, 18a being attached to the anchor pad 16, 16a as described above, may be positioned and secured on the patient near the insertion site for the medical article either before or after the placement of the catheter 12, 12a into the retainer. In many cases it will be desirable for the medical practitioner to attach the anchor pad 16, 16a and retainer 18, 18a to the patient prior to securing the medical article.

By way of illustration, the medical practitioner may first remove one portion of the release liner 52 from the anchor pad 16 by gripping the pull tab 56 (see FIG. 1) and pulling the liner 52 away from the lower surface 34 of the anchor pad 16. This exposes the adhesive layer of the anchor pad, which may then be applied to the skin of the patient near the site where the medical practitioner desires to secure the catheter 12. The remainder of the release liner 52 may then be removed and the securement device 14 fully attached to the skin of the patient. At this time, the covers 26, 28 of the retainer 18 may be opened and the catheter 12 secured to the retainer 18 as described above.

The various embodiments of anchoring systems and techniques described above in accordance with present invention thus provide a sterile, tight-gripping, needle- and tape-free way to anchor a medical article to a patient. The retainer thus eliminates use of tape, and if prior protocol required suturing, it also reduces the risk of accidental needle sticks, suture-wound-site infections and scarring. In addition, the techniques for the described retainers can be used with any of a wide variety of catheters, fittings, tubes, wires, and other medical articles. Patient comfort is also enhanced and application time is decreased with the use of the present anchoring system.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of different embodiments. For example, various bases, covers, posts, hinges, clips, anchor pads, and latching mechanisms disclosed herein, as well as other known equivalents for each such feature, can be mixed and matched by one of ordinary skill in this art to construct anchoring systems in accordance with principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims.

What is claimed is:

1. A securement system for anchoring a medical article to a body of a patient, the securement system comprising:
    a fitting attached to the medical article and having a pair of wings, each wing extending laterally beyond a body of the fitting;
    a securement device including a mounting surface for attaching the securement device to the patient's body; and
    a retainer being supported at least partially by the mounting surface and defining a receiving area, the retainer comprising a base and a plurality of clips that extend from the base, the clips being spaced apart by a distance that substantially equals a distance across a portion of the pair of wings of the fitting, each clip including an abutment section to abut against a corresponding outer edge of one of the pair of wings and a tang, the tang being disposed above the receiving area at a height equal to or greater than a transverse thickness of the pair of wings at a location along a longitudinal axis at the corresponding outer edge but less than a transverse thickness of a lateral cross section through the body at the location along the longitudinal axis, and at least two of the plurality of clips being disposed adjacent to a generally longitudinally facing surface of the pair of wings so as to prevent the fitting from being pulled through the securement device in both forward and backward longitudinal directions.

2. The securement system of claim 1, wherein the retainer additionally comprises at least one post that is sized to be inserted into an aperture of the fitting.

3. The securement system of claim 1, wherein the retainer further comprises at least one cover movable between an open position and a closed position, the cover extending over at least a portion of the fitting in the closed position when the fitting is engaged with at least one of the plurality of clips.

4. The securement system of claim 1, wherein the distance between the base and the tang generally matches the transverse thickness of the fitting at the corresponding edge.

5. The securement system of claim 1, wherein the plurality of clips comprises four clips arranged on the base so as to generally face edges of the fitting.

6. The securement system of claim 1, wherein at least one of the plurality of clips is arranged on the base so that the abutment section abuts a lateral facing surface of the fitting to thereby inhibit movement of the fitting in a lateral direction relative to the securement device.

7. The securement system of claim 1, wherein at least one of the plurality of clips is arranged on the base so that the abutment section abuts a longitudinal facing surface of the fitting to thereby inhibit movement of the fitting in a longitudinal direction relative to the securement device.

8. The securement system of claim 1, wherein the plurality of clips is arranged on the base so as to generally face the medical article.

9. A securement system comprising:
    a fitting attached to a medical article and having a pair of wings, each wing extending laterally beyond a body of the fitting;
    a mounting surface for attaching the securement device to the patient's body; and
    a retainer being supported at least partially by the mounting surface, the retainer comprising a base and a plurality of clips that extend from the base, the clips being spaced apart by a distance that substantially equals a distance across a portion of the pair of wings of the fitting, each clip including an abutment section to abut against a corresponding outer edge of one of the pair of wings and a tang, the tang being disposed above the base at a height equal to or greater than a transverse thickness of the pair of wings at a location along a longitudinal axis at the corresponding outer edge but less than a transverse thickness of a lateral cross section through the body at the location along the longitudinal axis, and at least two of the plurality of clips being disposed adjacent to a generally longitudinally facing surface of the pair of wings so as to prevent the fitting from being pulled through the securement device in both forward and backward longitudinal directions.

10. The securement system of claim 9, wherein each of the abutment sections abuts against a corresponding edge of the fitting.

11. The securement system of claim 9, wherein each tang is disposed above the base by a distance greater than a transverse thickness of the fitting at the corresponding edge.

12. The securement system of claim 9, wherein the retainer further comprises at least one cover movable between an open position and a closed position, the cover extending over at least a portion of the fitting in the closed position when the fitting is engaged with at least one of the plurality of clips.

13. The securement system of claim 9, wherein the plurality of clips comprises four clips arranged on the base so as to generally face edges of the fitting.

14. The securement system of claim 9, wherein the plurality of clips is arranged on the base so as to generally face the medical article.

15. The securement system of claim 9, wherein the plurality of clips is arranged on the receiving area so as to inhibit movement of the medical article in the longitudinal, transverse, and lateral directions relative to the securement device.

16. The securement system of claim 9, wherein the plurality of clips is arranged on the receiving area so as to abut both lateral and longitudinal surfaces of the medical article to thereby inhibit movement of the medical article in the longitudinal and lateral directions relative to the securement device.

17. The securement system of claim 9, wherein at least two of the plurality of clips are arranged on the receiving area so as to abut both lateral and longitudinal surfaces of the medical article to thereby inhibit movement of the medical article in the longitudinal and lateral directions relative to the securement device.

18. The securement system of claim 9, wherein the plurality of clips is arranged on the receiving area in two sets, each set facing towards the other set.

19. The securement system of claim 9 further comprising at least one post, the post interacting with the medical article.

20. The securement system of claim 9, wherein the at least one post is sized and shaped to pass through a hole in the medical article.

21. The securement system of claim 1, wherein the plurality of clips is arranged on the receiving area in two sets, each set facing towards the other set.

\* \* \* \* \*